United States Patent
Barta et al.

(10) Patent No.: US 11,944,619 B2
(45) Date of Patent: *Apr. 2, 2024

(54) PHENYLALANINE SMALL ORGANIC COMPOUNDS TO DIRECTLY MODULATE PCSK9 PROTEIN ACTIVITY

(71) Applicant: SRX Cardio, LLC, Pittsford, NY (US)

(72) Inventors: Thomas E. Barta, Carrboro, NC (US); Jonathan William Bourne, Fairport, NY (US); Kyle D. Monroe, Pittsford, NY (US); Michael M. Muehlemann, Liverpool, NY (US); Anjali Pandey, Fremont, CA (US); Simeon Bowers, Oakland, CA (US)

(73) Assignee: SRX Cardio, LLC, Pittsford, NY (US)

( * ) Notice: Subject to any disclaimer, the term of this patent is extended or adjusted under 35 U.S.C. 154(b) by 242 days.

This patent is subject to a terminal disclaimer.

(21) Appl. No.: 17/020,276

(22) Filed: Sep. 14, 2020

(65) Prior Publication Data

US 2021/0236481 A1 Aug. 5, 2021

Related U.S. Application Data

(63) Continuation of application No. 15/753,768, filed as application No. PCT/US2016/047810 on Aug. 19, 2016, now Pat. No. 10,821,106.

(60) Provisional application No. 62/298,852, filed on Feb. 23, 2016, provisional application No. 62/208,054, filed on Aug. 21, 2015.

(51) Int. Cl.
| | | |
|---|---|---|
| A61K 31/495 | (2006.01) | |
| A61K 31/4409 | (2006.01) | |
| A61K 45/06 | (2006.01) | |
| A61P 3/06 | (2006.01) | |
| C07C 237/20 | (2006.01) | |
| C07D 213/64 | (2006.01) | |

(52) U.S. Cl.
CPC ........ *A61K 31/495* (2013.01); *A61K 31/4409* (2013.01); *A61K 45/06* (2013.01); *A61P 3/06* (2018.01); *C07C 237/20* (2013.01); *C07D 213/64* (2013.01); *A61K 2300/00* (2013.01); *C07B 2200/07* (2013.01)

(58) Field of Classification Search
CPC ...... A61K 31/495; A61K 31/4409; A61P 3/06
See application file for complete search history.

(56) References Cited

U.S. PATENT DOCUMENTS

| | | | |
|---|---|---|---|
| 4,064,245 | A | 12/1977 | Beregi et al. |
| 5,236,934 | A | 8/1993 | VanAtten |
| 5,462,947 | A | 10/1995 | Svensson et al. |
| 5,863,903 | A | 1/1999 | Lundgren et al. |
| 5,866,513 | A | 2/1999 | Michelotti et al. |
| 7,750,012 | B2 | 7/2010 | Sandanayaka et al. |
| 8,673,850 | B2 | 3/2014 | Seidah et al. |
| 10,034,892 | B2 | 7/2018 | Barta et al. |
| 10,287,317 | B2 | 5/2019 | Muehlemann et al. |
| 10,307,433 | B2 | 6/2019 | Barta et al. |
| 10,568,882 | B2 | 2/2020 | Barta et al. |
| 10,688,114 | B2 | 6/2020 | Barta et al. |
| 10,821,106 | B2 | 11/2020 | Barta et al. |
| 10,865,185 | B2 | 12/2020 | Barta et al. |
| 10,980,801 | B2 | 4/2021 | Barta et al. |
| 2004/0082641 | A1 | 4/2004 | Rytved et al. |
| 2004/0254120 | A1 | 12/2004 | Fogleman et al. |
| 2007/0207985 | A1 | 9/2007 | Li et al. |
| 2008/0194621 | A1 | 8/2008 | Lang |
| 2009/0203676 | A1 | 8/2009 | Barba et al. |
| 2010/0113782 | A1 | 5/2010 | Bolin et al. |
| 2013/0064825 | A1 | 3/2013 | Chan et al. |
| 2014/0045854 | A1 | 2/2014 | Uesugi et al. |
| 2014/0093513 | A1 | 4/2014 | Milne et al. |
| 2015/0051144 | A1 | 2/2015 | Pingali et al. |
| 2015/0111857 | A1 | 4/2015 | Hodous et al. |
| 2019/0119236 | A1 | 4/2019 | Pandey et al. |

(Continued)

FOREIGN PATENT DOCUMENTS

| | | |
|---|---|---|
| EP | 0378207 | 7/1990 |
| EP | 2170866 | 12/2006 |

(Continued)

OTHER PUBLICATIONS

Annoura et al., "A Novel Class of Na+ and Ca2+ Channel Dual Blockers with Highly Potent Ani-Ischemic Effects", Bioorganic and Medicinal Chemistry Letters 9 (1999), pp. 2999-3002.

(Continued)

*Primary Examiner* — Alicia L Otton

(74) *Attorney, Agent, or Firm* — Sheppard Mullin Richter & Hampton LLP

(57) ABSTRACT

This invention is related to the field of PCSK9 biology and the composition and methods of use of small organic compounds as ligands for modulation of PCSK9 biological activity. In particular, the invention provides compositions of small organic compounds that modulate circulating levels of low density lipoproteins by altering the conformation of the protein PCSK9. Binding these small organic compound ligands to PCSK9 alters the conformation of the protein, modifying the interaction between PCSK9 and an endogenous low density lipoprotein receptor, and can lead to reduced or increased levels of circulating LDL-cholesterol. High LDL-cholesterol levels are associated with increased risk for heart disease. Low LDL-cholesterol levels may be problematic in other conditions, such as liver dysfunction; thus, there is also utility for small organic compound ligands that can raise LDL levels.

17 Claims, 2 Drawing Sheets

Specification includes a Sequence Listing.

(56) References Cited

U.S. PATENT DOCUMENTS

| | | |
|---|---|---|
| 2021/0032214 A1 | 2/2021 | Pandey et al. |
| 2021/0309613 A1 | 10/2021 | Barta et al. |
| 2022/0047582 A1 | 2/2022 | Barta et al. |
| 2022/0193058 A1 | 6/2022 | Bowers et al. |
| 2022/0267269 A1 | 8/2022 | Bowers et al. |

FOREIGN PATENT DOCUMENTS

| | | |
|---|---|---|
| EP | 1987827 | 11/2008 |
| WO | WO 92/02501 | 2/1992 |
| WO | WO 1995/000161 | 1/1995 |
| WO | WO 1999/002502 | 1/1999 |
| WO | WO 1999/028313 | 10/2000 |
| WO | WO 01/96301 | 12/2001 |
| WO | WO 02/36123 | 5/2002 |
| WO | WO 2003/072558 | 9/2003 |
| WO | WO 2004/043929 | 5/2004 |
| WO | WO 2004/060882 | 7/2004 |
| WO | WO 2004/069792 | 8/2004 |
| WO | WO 2005/000309 | 1/2005 |
| WO | WO 2005/115361 | 12/2005 |
| WO | WO 2006/049597 | 5/2006 |
| WO | WO 2006/125665 | 11/2006 |
| WO | WO 2007/009741 | 1/2007 |
| WO | WO 2009/002469 | 12/2008 |
| WO | WO 2011/051961 | 5/2011 |
| WO | WO 2012/039660 | 3/2012 |
| WO | WO 2012/154760 | 11/2012 |
| WO | WO 2014/101120 | 7/2014 |
| WO | WO 2014/101373 | 7/2014 |
| WO | WO 2014/105666 | 7/2014 |
| WO | WO 2014/127316 | 8/2014 |
| WO | WO 2014/128198 | 8/2014 |
| WO | WO 2014/150395 | 9/2014 |
| WO | WO 2014/150983 | 9/2014 |
| WO | WO 2015/024016 | 2/2015 |
| WO | WO 2016/029307 | 2/2016 |
| WO | WO 2016/107602 | 7/2016 |
| WO | WO 2016/107603 | 7/2016 |
| WO | WO 2017/100726 | 6/2017 |
| WO | WO 2018/026866 | 2/2018 |
| WO | WO 2018/165718 | 9/2018 |
| WO | WO 2020/252383 | 12/2020 |

OTHER PUBLICATIONS

CAS Registry No. 57536-86-4; entry dated Mar. 25, 2005.
Database Registry, Chemical Abstracts Service, XP002768756, retrieved from STN Database accession No. 1770149-41-1, Jun. 1, 2015.
Database Registry, Chemical Abstracts Service, XP002768757, retrieved from STN Database accession No. 1796858-42-8, Jul. 8, 2015.
Extended European Search Report for EP Appln. No. 16839887.3 dated Jan. 2, 2019, 8 pages.
Extended European Search Report for EP Appln. No. 16839890.7 dated Mar. 20, 2019, 4 pages.
Extended European Search Report for EP Appln. No. 16839893.1 dated Feb. 15, 2019, 10 pages.
International Search Report and Written Opinion for PCT/US2016/047816 dated Nov. 16, 2016, 8 pages.
International Search Report and Written Opinion for PCT/US2016/047810 dated Nov. 16, 2016, 7 pages.
International Search Report and Written Opinion for PCT/US2016/019189 dated Jul. 24, 2017, 13 pages.
International Search Report and Written Opinion for PCT/US2016/047798 dated Jan. 13, 2017, 10 pages.
Luhn et al., "Dissolution Profile of Novel Composite Pellet Cores Based on Different Ratios of Microcrystalline Cellulose and Isomalt", Journal of Pharmaceutical Sciences, vol. 101, Issue 8, pp. 2675-2680, 2012.
Pubchem CID 14819316 Create Date: Feb. 9, 2007. Retrieved from the Internet: <URL: https://pubchem. ncbi .nlm.nih.gov/compound/14819316>.
Pubchem-CID 73012351 Date Created: Mar. 7, 2014, p. 3 figure listed. Retrieved from the Internet: URL: https://pubchem.ncbi.nlm.nih.oov/compound/73012351.
Pubchem CID 23519490 Create Date: Dec. 6, 2007 Date Accessed: Oct. 20, 2016, p. 3, compound listed. Retrieved from the Internet: URL:https://pubchem.ncbi.nim.nih.gov/compound/23519490@section=Top.
Pubchem CID 28917034 Create Date: May 28, 2009 p. 3, Fig. Retrieved from the Internet: <URL: https://pubchem.ncbi.nim.nih.gov/compound/28917034>.
Pubchem CID 73012351 Create Date: Mar. 7, 2014 p. 3, figure listed. Retrieved from the Internet: <URL: https://pubchem.ncbi.nlm.nih.gov/compound/73012351>.
Sam et al., "Phenylisoquinolines and Hydroisoquinolines", Journal of Pharmaceutical Sciences, vol. 59, No. 1, pp. 59-62, 1970.
STN Registry database for CAS RN 758671-90-8, entry date of Oct. 8, 2004, accessed Sep. 26, 2019.
STN Registry database entry for CAS RN 769101-76-0, entry date of Oct. 26, 2004, Accessed Feb. 18, 2020.
Banker, et al., (1996), Modern Pharmaceuticals, p. 596.
International Search Report and Written Opinion in International Patent Application No. PCT/US2020/037591, dated Feb. 3, 2021. 10 pages.
Le Bourdonnec et al. Synthesis and Pharmacological Evaluation of Novel Octahydro-1H-pyrido[1,2-a]pyrazine as μ-Opioid Receptor Antagonists. Journal of Medicinal Chemistry, 49(25), 7290-7306 (2006).
Pubchem. CID 135243294. Dec. 15, 2018, pp. 1-9. Retrieved from the Internet <URL: https://pubchem.ncbi.nlm.nih.gov/compound/135243294>; p. 2, formula.
Pubchem. 84050476. Oct. 20, 2014, pp. 1-8. Retrieved from the Internet <URL: https://pubchem.ncbi.nlm.nih.gov/compound/84050476>; p. 2, formula.
Wolff et al., "Burger's Medicinal Chemistry and Drug Discovery," 5th Ed. Part 1, pp. 975-977 (1995).

PHENYLALANINE SMALL ORGANIC COMPOUNDS TO DIRECTLY MODULATE PCSK9 PROTEIN ACTIVITY

This application is a Continuation of U.S. application Ser. No. 15/753,768, filed on Feb. 20, 2018, which is a U.S. National Stage Application under 35 U.S.C. § 371 of International Application No. PCT/US2016/047810, filed Aug. 19, 2016, which claims priority benefit of U.S. Provisional Patent Application No. 62/298,852 filed on Feb. 23, 2016 and U.S. Provisional Patent Application No. 62/208,054 filed on Aug. 21, 2015.

FIELD OF INVENTION

This invention is related to the field of PCSK9 biology. In particular, the invention provides compositions and methods of use of small organic compounds as ligands that directly bind with the PCSK9 protein, and differentially modify PCSK9 biological activity in cells. These changes may include alteration in PCSK9 binding to, or dissociating from, LDLR, changes in LDLR number on the cell surface, or changes in the rate of LDL internalization.

SEQUENCE LISTING

The instant application contains a Sequence Listing which has been filed electronically in ASCII format and is hereby incorporated by reference in its entirety. Said ASCII copy, created on Nov. 16, 2016, is named 69TJ-267795-US_SL.txt and is 6,591 bytes in size.

BACKGROUND

Elevated plasma levels of low density lipoprotein cholesterol (LDL-C) represent the greatest risk factor for the development of coronary heart disease. Clearance of LDL-C from the plasma occurs primarily by the liver through the action of LDL receptors (LDLRs), which are cell surface glycoproteins that bind to apolipoprotein B100 (apoB100) on LDL particles with high affinity and mediate their endocytic uptake. Goldstein et al., *Annu. Rev. Cell Biol.* 1:1-39 (1985). Autosomal dominant hypercholesterolemia (ADH) is associated with mutations that reduce plasma LDL clearance that are found in genes encoding the LDLR (familial hypercholesterolemia (FH)) or apoB100 (familial defective apoB100). Hobbs et al., *Annu. Rev. Genet.* 24, 133-170 (1990); and Innerarity et al., *J. Lipid Res.* 31:1337-1349 (1990), respectively.

The low density lipoprotein (LDL) receptor (LDLR) mediates efficient endocytosis of VLDL, VLDL remnants, and LDL. As part of the endocytic process, the LDLR releases lipoproteins into hepatic endosomes.

One approach to modulating LDL-cholesterol levels would be to identify small organic compounds that bind to PCSK9 and alter the kinetics of the interaction between PCSK9 and the LDLR such that the rate of lipoprotein clearance by LDLR endocytosis is increased or decreased, as desired.

SUMMARY OF THE INVENTION

This invention is related to the field of PCSK9 biology and treatment of hypercholesterolemia and hypocholesterolemia. In particular, the invention provides compositions of ligands that bind and alter PCSK9 biological conformation and methods that use these ligands to modify PCSK9 activity to change circulating levels of low density lipoprotein in the blood. These ligands may be small organic compounds, and more preferably small organic compounds less than 600 Da. Altering the conformation of PCSK9 can change the interactions between PCSK9 and an endogenous low density lipoprotein receptor, and can lead to reduced or increased levels of circulating LDL-cholesterol. High LDL-cholesterol levels are associated with increased risk for heart disease. Low LDL-cholesterol levels may be problematic in other conditions, such as liver dysfunction; thus, there is also utility for ligands that can raise LDL levels.

Phenylalanine Scaffold:

In one embodiment, the present invention contemplates a phenylalanine small organic compound comprising of a phenylalanine scaffold of Formula I:

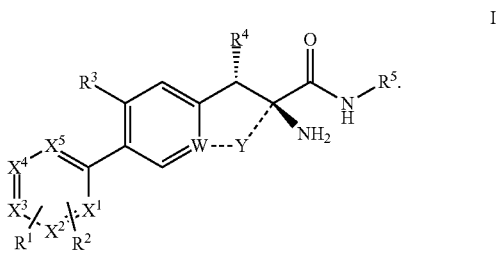

wherein i) $R^1$ and $R^2$ are independently selected from the group consisting of, H, lower alkyl, halogen, —OH, oxo, amino; ii) $R^3$ is selected from the group consisting of H, lower alkyl, halogen haloalkyl, hydroxylalkyl, alkoxyl, nitrile; iii) $R^4$ is selected from the group consisting of H and —OH; iv) $R^5$ is selected from the group consisting of alkyl, lower alkyl, branched alkyl, aryl substituted alkyl, cycloalkyl, hydroxyalkyl, alkoxyalkyl, haloalkyl, and an amino acid, wherein the amino acid is an L- or D-isomer of the formula —$CHR^6$—CON—$R^7$ wherein i) $R^6$ is selected from the group consisting of natural or unnatural peptide side chains; ii) $R^7$ is selected from the group consisting of alkyl, lower alkyl, branched alkyl, cycloalkyl, and heterocycle; v) $X^1$ through $X^5$ are selected independently from the group of C and N; vi) W is C, CH, or N, wherein when W is C then a saturated 5 member ring may optionally be constructed from Y as $CH_2$. Also provided are pharmaceutically acceptable salts, hydrates, solvates, tautomeric forms, and stereoisomers of these compounds. In one embodiment the small organic compound is selected from the group comprising of:

(S)-3-([1,1'-biphenyl]-4-yl)-2-amino-N-isopropylpropanamide;
(S)-3-([1,1'-biphenyl]-4-yl)-2-amino-N-butylpropanamide;
(S)-2-amino-3-(3-fluoro-4-(pyridin-4-yl)phenyl)-N-isopropylpropanamide;
(S)-2-amino-N-isopropyl-3-(3-methyl-4-(2-oxo-1,2-dihydropyridin-4-yl)phenyl)propanamide;
(S)-2-amino-3-(3'-hydroxy-2-methyl-[1,1'-biphenyl]-4-yl)-N-isopropylpropanamide;
(2S,3R)-2-amino-3-hydroxy-3-(5-(3-hydroxyphenyl)-4-methylpyridin-2-yl)-N-isopropylpropanamide;
(S)-2-amino-3-(5-(3-hydroxyphenyl)pyridin-2-yl)-N-isopropylpropanamide;
(S)-2-amino-3-(5-(3-hydroxyphenyl)-4-methylpyridin-2-yl)-N-isopropylpropanamide;
(S)-2-amino-3-(2'-fluoro-5'-hydroxy-2-methyl-[1,1'-biphenyl]-4-yl)-N-isopropylpropanamide;
(R)-2-amino-N-isopropyl-5-phenyl-2,3-dihydro-1H-indene-2-carboxamide;

(S)-3-([1,1'-biphenyl]-4-yl)-2-amino-N—((S)-1-(isopropylamino)-1-oxopropan-2-yl)propanamide;
(S)-3-([1,1'-biphenyl]-4-yl)-2-amino-N—((R)-1-(isopropylamino)-1-oxopropan-2-yl)propanamide;
(R)-2-((S)-3-([1,1'-biphenyl]-4-yl)-2-aminopropanamido)-N-ethyl-3-methylbutanamide;
(S)-3-([1,1'-biphenyl]-4-yl)-2-amino-N—((S)-1-(((S)-1-morpholino-1-oxopropan-2-yl)amino)-1-oxopropan-2-yl)propanamide;
(S)-2-amino-3-(3'-hydroxy-[1,1'-biphenyl]-4-yl)-N—((S)-1-(isopropylamino)-1-oxopropan-2-yl)propanamide;
(R)-2-amino-5-(3-hydroxyphenyl)-N-isopropyl-6-methyl-2,3-dihydro-1H-indene-2-carboxamide;
(S)-2-amino-N-isopropyl-3-(4-(2-oxo-1,2-dihydropyridin-4-yl)phenyl)propanamide;
(S)-2-amino-3-(3'-hydroxy-[1,1'-biphenyl]-4-yl)-N-isopropylpropanamide;
(S)-3-([1,1'-biphenyl]-4-yl)-2-amino-N-cyclopentylpropanamide;
(S)-3-([1,1'-biphenyl]-4-yl)-2-amino-N—((R)-1-phenylpropan-2-yl)propanamide;
(S)-3-([1,1'-biphenyl]-4-yl)-2-amino-N—((S)-1-phenylpropan-2-yl)propanamide;
(S)-2-amino-3-(2-cyano-[1,1'-biphenyl]-4-yl)-N-isopropylpropanamide;
(S)-2-amino-N-isopropyl-3-(2-methoxy-[1,1'-biphenyl]-4-yl)propanamide;
(S)-2-amino-N-isopropyl-3-(2-(trifluoromethyl)-[1,1'-biphenyl]-4-yl)propanamide;
(S)-2-amino-3-(2',3'-difluoro-[1,1'-biphenyl]-4-yl)-N-isopropylpropanamide;
(S)-2-amino-3-(2-ethyl-[1,1'-biphenyl]-4-yl)-N-isopropylpropanamide;
(S)-2-amino-3-(4-cyclohexylphenyl)-N-isopropylpropanamide;
(S)-2-amino-N-isopropyl-3-(4-(thiophen-2-yl)phenyl)propanamide;
and (S)-2-amino-3-(4-cyclopentylphenyl)-N-isopropylpropanamide;
or a pharmaceutical composition thereof.

In one embodiment, the present invention contemplates a phenylalanine small organic compound comprising of a phenylalanine scaffold of Formula II:

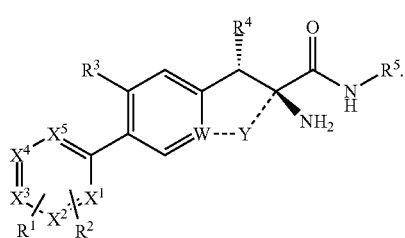

II wherein i) $R^1$ and $R^2$ are independently selected from the group consisting of, H, lower alkyl, halogen, —OH, oxo, amino; ii) $R^3$ is selected from the group consisting of H, lower alkyl, halogen; iii) $R^4$ is selected from the group consisting of H and —OH; iv) $R_5$ is selected from the group consisting of alkyl, lower alkyl, hydroxyalkyl, alkoxyalkyl, and haloalkyl v) $X^1$ through $X^5$ are selected independently from the group of either C and N; vi) W is C or N, where if W is C then a saturated 5 member ring may optionally be constructed from Y as CH2.

Compound Methods of Use:

In one embodiment, the present invention contemplates a method, comprising: a) providing; i) a PCSK9 protein, wherein said protein comprises a binding site that induces allosteric modulation and a low density lipoprotein receptor binding site; ii) a small organic compound capable of binding to said binding site, and selected from the group consisting of a compound of a phenylalanine scaffold of Formula I; iii) a plurality of hepatocyte cells comprising a low density lipoprotein receptor and low density lipoproteins; b) binding said small organic compound to said binding site, wherein said small organic compound induces a conformational shift of said protein; and c) modulating the rate of low density lipoprotein receptor internalization by said plurality of hepatocytes by said conformational shift. In one embodiment the present invention contemplates a method, wherein said small organic compound induces a conformational change of the PCSK9 protein, such that the rate of low density lipoprotein receptor internalization by a plurality of hepatocytes is increased. In one embodiment, the present invention contemplates a method, wherein said small organic compound induces a conformational change of the PCSK9 protein, such that the rate of low density lipoprotein internalization by a plurality of hepatocytes is increased.

In one embodiment, the present invention contemplates a method, comprising: a) providing; i) a PCSK9 protein, wherein said protein comprises a binding site that induces allosteric modulation and a low density lipoprotein receptor binding site; ii) a small organic compound capable of binding to said binding site, and selected from the group consisting of a compound of a phenylalanine scaffold of Formula I; iii) a plurality of hepatocyte cells comprising a low density lipoprotein receptor and low density lipoproteins; b) binding said small organic compound to said binding site, wherein said small organic compound induces a conformational shift of said protein; and c) modulating the affinity of said low density lipoprotein receptor binding site for said low density lipoprotein receptor by said conformational shift.

In one embodiment, the small organic compound is an allosteric inhibitor ligand wherein said modulating decreases the affinity of said low density lipoprotein receptor binding site for said low density lipoprotein receptor such that internalization of said low density lipoprotein by said plurality of hepatocytes is increased. In one embodiment, the conformational shift of said protein is selected from the group consisting of an induced fit shift and a biomechanical shift. In one embodiment the small organic compound is a small molecule compound. In one embodiment, the small organic compound is selected from the group consisting of a phenylalanine scaffold of Formula I. Also provided are pharmaceutically acceptable salts, hydrates, solvates, tautomeric forms, and stereoisomers of these compounds selected from the group consisting of a phenylalanine scaffold of Formula I.

In one embodiment, the small organic compound is an allosteric inhibitor ligand wherein said modulating decreases the affinity of said low density lipoprotein receptor binding site for said low density lipoprotein receptor such that internalization of said low density lipoprotein by said plurality of hepatocytes is increased. In one embodiment, the conformational shift of said protein is selected from the group consisting of an induced fit shift and a biomechanical shift. In one embodiment the small organic compound is a small molecule compound. In one embodiment, the small organic compound is selected from the group comprising of:

(S)-3-([1,1'-biphenyl]-4-yl)-2-amino-N-isopropylpropanamide;
(S)-3-([1,1'-biphenyl]-4-yl)-2-amino-N-butylpropanamide;
(S)-2-amino-3-(3-fluoro-4-(pyridin-4-yl)phenyl)-N-isopropylpropanamide;
(S)-2-amino-N-isopropyl-3-(3-methyl-4-(2-oxo-1,2-dihydropyridin-4-yl)phenyl)propanamide;
(S)-2-amino-3-(3'-hydroxy-2-methyl-[1,1'-biphenyl]-4-yl)-N-isopropylpropanamide; (2S,3R)-2-amino-3-hydroxy-3-(5-(3-hydroxyphenyl)-4-methylpyridin-2-yl)-N-isopropylpropanamide;
(S)-2-amino-3-(5-(3-hydroxyphenyl)pyridin-2-yl)-N-isopropylpropanamide;
(S)-2-amino-3-(5-(3-hydroxyphenyl)-4-methylpyridin-2-yl)-N-isopropylpropanamide;
(S)-2-amino-3-(2'-fluoro-5'-hydroxy-2-methyl-[1,1'-biphenyl]-4-yl)-N-isopropylpropanamide;
(R)-2-amino-N-isopropyl-5-phenyl-2,3-dihydro-1H-indene-2-carboxamide;
(S)-3-([1,1'-biphenyl]-4-yl)-2-amino-N—((S)-1-(isopropylamino)-1-oxopropan-2-yl)propanamide;
(S)-3-([1,1'-biphenyl]-4-yl)-2-amino-N—((R)-1-(isopropylamino)-1-oxopropan-2-yl)propanamide;
(R)-2-((S)-3-([1,1'-biphenyl]-4-yl)-2-aminopropanamido)-N-ethyl-3-methylbutanamide;
(S)-3-([1,1'-biphenyl]-4-yl)-2-amino-N—((S)-1-(((S)-1-morpholino-1-oxopropan-2-yl)amino)-1-oxopropan-2-yl)propanamide;
(S)-2-amino-3-(3'-hydroxy-[1,1'-biphenyl]-4-yl)-N—((S)-1-(isopropylamino)-1-oxopropan-2-yl)propanamide;
(R)-2-amino-5-(3-hydroxyphenyl)-N-isopropyl-6-methyl-2,3-dihydro-1H-indene-2-carboxamide;
(S)-2-amino-N-isopropyl-3-(4-(2-oxo-1,2-dihydropyridin-4-yl)phenyl)propanamide;
(S)-2-amino-3-(3'-hydroxy-[1,1'-biphenyl]-4-yl)-N-isopropylpropanamide;
(S)-3-([1,1'-biphenyl]-4-yl)-2-amino-N-cyclopentylpropanamide;
(S)-3-([1,1'-biphenyl]-4-yl)-2-amino-N—((R)-1-phenylpropan-2-yl)propanamide;
(S)-3-([1,1'-biphenyl]-4-yl)-2-amino-N—((S)-1-phenylpropan-2-yl)propanamide;
(S)-2-amino-3-(2-cyano-[1,1'-biphenyl]-4-yl)-N-isopropylpropanamide;
(S)-2-amino-N-isopropyl-3-(2-methoxy-[1,1'-biphenyl]-4-yl)propanamide;
(S)-2-amino-N-isopropyl-3-(2-(trifluoromethyl)-[1,1'-biphenyl]-4-yl)propanamide;
(S)-2-amino-3-(2',3'-difluoro-[1,1'-biphenyl]-4-yl)-N-isopropylpropanamide;
(S)-2-amino-3-(2-ethyl-[1,1'-biphenyl]-4-yl)-N-isopropylpropanamide;
(S)-2-amino-3-(4-cyclohexylphenyl)-N-isopropylpropanamide;
(S)-2-amino-N-isopropyl-3-(4-(thiophen-2-yl)phenyl)propanamide;
and (S)-2-amino-3-(4-cyclopentylphenyl)-N-isopropylpropanamide;
or a pharmaceutical composition thereof.

In one embodiment, the present invention contemplates, a method, comprising: a) providing; i) a PCSK9 protein, wherein said protein comprises a binding site that induces allosteric modulation and a low density lipoprotein receptor binding site; ii) a small organic compound capable of binding said binding site, and selected from the group consisting of a compound of a phenylalanine scaffold of Formula I; iii) a plurality of hepatocyte cells comprising a population of low density lipoprotein receptors; b) binding said small organic compound to said binding site, wherein said small organic compound induces a conformational shift of said protein; c) modulating said population of said low density lipoprotein receptors by said conformational shift. In one embodiment the present invention contemplates a method, wherein said small organic compound induces a conformational change of the PCSK9 protein, such that the population of low density lipoprotein receptors is increased.

In one embodiment, the small organic compound is an allosteric inhibitor ligand wherein said small molecule ligand induces a conformational change of the PCSK9 protein, such that the population of low density lipoprotein receptors is increased. In one embodiment, the small organic compound is an allosteric inhibitor ligand wherein said modulating increases said population of said low density lipoprotein receptors measurable on the cell surface of said plurality of hepatocytes. In one embodiment, the conformational shift of said protein is selected from the group consisting of an induced fit shift and a biomechanical shift. In one embodiment the small molecule compound is an organic chemical compound. In one embodiment, the small organic compound is selected from the group consisting of a phenylalanine scaffold of Formula I. Also provided are pharmaceutically acceptable salts, hydrates, solvates, tautomeric forms, and stereoisomers of these compounds selected from the group consisting of a phenylalanine scaffold of Formula I.

In one embodiment, the small organic compound is an allosteric inhibitor ligand wherein said small molecule ligand induces a conformational change of the PCSK9 protein, such that the population of low density lipoprotein receptors is increased. In one embodiment, the small organic compound is an allosteric inhibitor ligand wherein said modulating increases said population of said low density lipoprotein receptors measurable on the cell surface of said plurality of hepatocytes. In one embodiment, the conformational shift of said protein is selected from the group consisting of an induced fit shift and a biomechanical shift. In one embodiment the small molecule compound is an organic chemical compound. In one embodiment, the small organic compound is selected from the group comprising of:
(S)-3-([1,1'-biphenyl]-4-yl)-2-amino-N-isopropylpropanamide;
(S)-3-([1,1'-biphenyl]-4-yl)-2-amino-N-butylpropanamide;
(S)-2-amino-3-(3-fluoro-4-(pyridin-4-yl)phenyl)-N-isopropylpropanamide;
(S)-2-amino-N-isopropyl-3-(3-methyl-4-(2-oxo-1,2-dihydropyridin-4-yl)phenyl)propanamide;
(S)-2-amino-3-(3'-hydroxy-2-methyl-[1,1'-biphenyl]-4-yl)-N-isopropylpropanamide;
(2S,3R)-2-amino-3-hydroxy-3-(5-(3-hydroxyphenyl)-4-methylpyridin-2-yl)-N-isopropylpropanamide;
(S)-2-amino-3-(5-(3-hydroxyphenyl)pyridin-2-yl)-N-isopropylpropanamide;
(S)-2-amino-3-(5-(3-hydroxyphenyl)-4-methylpyridin-2-yl)-N-isopropylpropanamide;
(S)-2-amino-3-(2'-fluoro-5'-hydroxy-2-methyl-[1,1'-biphenyl]-4-yl)-N-isopropylpropanamide;
(R)-2-amino-N-isopropyl-5-phenyl-2,3-dihydro-1H-indene-2-carboxamide;
(S)-3-([1,1'-biphenyl]-4-yl)-2-amino-N—((S)-1-(isopropylamino)-1-oxopropan-2-yl)propanamide;
(S)-3-([1,1'-biphenyl]-4-yl)-2-amino-N—((R)-1-(isopropylamino)-1-oxopropan-2-yl)propanamide;
(R)-2-((S)-3-([1,1'-biphenyl]-4-yl)-2-aminopropanamido)-N-ethyl-3-methylbutanamide;

(S)-3-([1,1'-biphenyl]-4-yl)-2-amino-N—((S)-1-(((S)-1-morpholino-1-oxopropan-2-yl)amino)-1-oxopropan-2-yl)propanamide;
(S)-2-amino-3-(3'-hydroxy-[1,1'-biphenyl]-4-yl)-N—((S)-1-(isopropylamino)-1-oxopropan-2-yl)propanamide;
(R)-2-amino-5-(3-hydroxyphenyl)-N-isopropyl-6-methyl-2,3-dihydro-1H-indene-2-carboxamide;
(S)-2-amino-N-isopropyl-3-(4-(2-oxo-1,2-dihydropyridin-4-yl)phenyl)propanamide;
(S)-2-amino-3-(3'-hydroxy-[1,1'-biphenyl]-4-yl)-N-isopropylpropanamide;
(S)-3-([1,1'-biphenyl]-4-yl)-2-amino-N-cyclopentylpropanamide;
(S)-3-([1,1'-biphenyl]-4-yl)-2-amino-N—((R)-1-phenylpropan-2-yl)propanamide;
(S)-3-([1,1'-biphenyl]-4-yl)-2-amino-N—((S)-1-phenylpropan-2-yl)propanamide;
(S)-2-amino-3-(2-cyano-[1,1'-biphenyl]-4-yl)-N-isopropylpropanamide;
(S)-2-amino-N-isopropyl-3-(2-methoxy-[1,1'-biphenyl]-4-yl)propanamide;
(S)-2-amino-N-isopropyl-3-(2-(trifluoromethyl)-[1,1'-biphenyl]-4-yl)propanamide;
(S)-2-amino-3-(2',3'-difluoro-[1,1'-biphenyl]-4-yl)-N-isopropylpropanamide;
(S)-2-amino-3-(2-ethyl-[1,1'-biphenyl]-4-yl)-N-isopropylpropanamide;
(S)-2-amino-3-(4-cyclohexylphenyl)-N-isopropylpropanamide;
(S)-2-amino-N-isopropyl-3-(4-(thiophen-2-yl)phenyl)propanamide;
and (S)-2-amino-3-(4-cyclopentylphenyl)-N-isopropylpropanamide;
or a pharmaceutical composition thereof.

In one embodiment, the present invention contemplates a compound including, but not limited to, a phenylalanine scaffold of Formula I. In one embodiment, the PCSK9 binding small organic ligand is selected from the group consisting of: a phenylalanine scaffold of Formula I. In one embodiment, the compound is formulated as a pharmaceutical composition. In one embodiment, the pharmaceutical composition further comprises a pharmaceutical drug. In one embodiment, the pharmaceutical drug is selected from the group consisting of a statin, a cardiovascular drug, a metabolic drug, and an antihypertensive drug. In one embodiment, the pharmaceutical drug is selected from the group consisting of ezetimibe, amlodipine besylate, sitagliptin, metformin, atorvastatin, rosuvastatin and simvastatin. In one embodiment, the pharmaceutical composition is formulated as selected from the group consisting of a tablet, a liquid, a gel, a capsule, a sachet, a microparticle, a liposome, a nanoparticle, a salt, a transdermal patch, an ointment, a lotion, a cream, a gel, a drop, a strip, a suppository, a spray and a powder.

In one embodiment, the present invention contemplates a composition comprising a PCSK9 allosteric small organic compound selected from the group comprising of a phenylalanine scaffold of Formula I as a small molecule ligand. In one embodiment, the composition is a pharmaceutical composition. In one embodiment, the pharmaceutical composition comprises an effective dose of said ligand. In one embodiment, the pharmaceutical composition comprises salts. In one embodiment, the pharmaceutical composition is formulated for oral administration.

In one embodiment, the present invention contemplates a method, comprising: a) administering to a subject a small organic compound selected from the group consisting of a phenylalanine scaffold of Formula I, which binds PCSK9 and is an allosteric modulator of the protein, wherein said subject has at least one symptom of a cardiovascular disease; and b) reducing said at least one symptom of cardiovascular disease by said PCSK9 allosteric modulator small molecule compound administration. In one embodiment, said at least one symptom is reduced between 10-85%. In one embodiment, said at least one symptom is reduced between 20-65%. In one embodiment, said at least one symptom is reduced between 30-55%. In one embodiment, the cardiovascular disease comprises a coronary disease. In one embodiment, the cardiovascular disease comprises hypertension. In one embodiment, the cardiovascular disease comprises hypercholesterolemia. In one embodiment, the cardiovascular disease comprises atherosclerosis. In one embodiment, the at least one symptom comprises reduced circulating high density lipoprotein. In one embodiment, the at least one symptom comprises elevated circulating cholesterol. In one embodiment, the at least one symptom comprises elevated circulating low density lipoprotein. In one embodiment, the at least one symptom comprises high blood pressure. In one embodiment, the administering comprises an effective dose of said PCSK9 allosteric modulator small organic compound. In one embodiment, said administering further comprises a delivery system selected from the group including, but not limited to, liposomes, microparticles and nanoparticles. In one embodiment, the effective dose comprises a pharmaceutical composition. In one embodiment, the pharmaceutical composition comprises salts. In one embodiment, the pharmaceutical composition is formulated for oral administration. In one embodiment the allosteric modulator small organic compound is an organic chemical compound small molecule. In one embodiment, the small organic compound is selected from the group consisting of a phenylalanine scaffold of Formula I.

In one embodiment, the present invention contemplates a method, comprising: a) administering a PCSK9 allosteric small organic compound selected from the group consisting of a phenylalanine scaffold of Formula I to a subject, wherein said subject has at least one symptom of a liver disease; and b) reducing said at least one symptom of liver disease by said PCSK9 allosteric small molecule administration. In one embodiment, the at least one symptom comprises elevated low density lipoprotein receptor density. In one embodiment the at least one symptom comprises reduced low density lipoprotein receptor density. In one embodiment, said at least one symptom is reduced between 10-85%. In one embodiment, said at least one symptom is reduced between 20-65%. In one embodiment, said at least one symptom is reduced between 30-55%. In one embodiment, the PCSK9 allosteric small organic compound comprises a PCSK9 allosteric inhibitor compound. In one embodiment, the administering comprises an effective dose of said PCSK9 allosteric inhibitor compound. In one embodiment, said administering further comprises a delivery system selected from the group including, but not limited to, liposomes, microparticles and nanoparticles. In one embodiment, the effective dose comprises a pharmaceutical composition. In one embodiment, the pharmaceutical composition comprises salts. In one embodiment, the pharmaceutical composition is formulated for oral administration. In one embodiment the small organic compound is an organic chemical compound small molecule. In one embodiment, the small organic compound is selected from the group consisting of a phenylalanine scaffold of Formula I.

In one embodiment, the present invention contemplates a method, comprising: a) administering a PCSK9 allosteric small organic compound selected from the group consisting of a phenylalanine scaffold of Formula I to a subject, wherein said subject has at elevated PCSK9 protein levels in the blood; and b) reducing said at least one symptom of elevated PCSK9 by said PCSK9 allosteric small molecule compound administration. In one embodiment, the at least one symptom comprises reduced low density lipoprotein receptor density. In one embodiment, said at least one symptom is reduced between 10-85%. In one embodiment, said at least one symptom is reduced between 20-65%. In one embodiment, said at least one symptom is reduced between 30-55%. In one embodiment, the PCSK9 allosteric small molecule compound comprises a PCSK9 allosteric inhibitor compound. In one embodiment, the administering comprises an effective dose of said PCSK9 allosteric small molecule compound. In one embodiment, said administering further comprises a delivery system selected from the group including, but not limited to, liposomes, microparticles and nanoparticles. In one embodiment, the effective dose comprises a pharmaceutical composition. In one embodiment, the pharmaceutical composition comprises salts. In one embodiment, the pharmaceutical composition is formulated for oral administration. In one embodiment the small molecule compound is an organic chemical compound. In one embodiment, the small organic compound is selected from the group consisting of a phenylalanine scaffold of Formula I.

In one embodiment, the present invention contemplates a method, comprising: a) administering a PCSK9 allosteric small organic compound selected from the group consisting of a phenylalanine scaffold of Formula I to a subject, wherein said subject has at below-average PCSK9 protein levels in the blood; and b) reducing said at least one symptom of elevated PCSK9 by said PCSK9 allosteric small molecule compound administration. In one embodiment, the at least one symptom comprises elevated low density lipoprotein receptor density. In one embodiment, said at least one symptom is reduced between 10-85%. In one embodiment, said at least one symptom is reduced between 20-65%. In one embodiment, said at least one symptom is reduced between 30-55%. In one embodiment, the PCSK9 allosteric small molecule compound comprises a PCSK9 allosteric activator compound. In one embodiment, the administering comprises an effective dose of said PCSK9 allosteric small molecule compound. In one embodiment, said administering further comprises a delivery system selected from the group including, but not limited to, liposomes, microparticles and nanoparticles. In one embodiment, the effective dose comprises a pharmaceutical composition. In one embodiment, the pharmaceutical composition comprises salts. In one embodiment, the pharmaceutical composition is formulated for oral administration. In one embodiment the small molecule compound is an organic chemical compound. In one embodiment, the small organic compound is selected from the group consisting of a phenylalanine scaffold of Formula I.

In one embodiment, the present invention further contemplates a kit comprising (a) a first container comprising a pharmaceutical composition of a small organic compound of Formula I; and (b) instructions for the use thereof for treatment of hypercholesterolemia. In one embodiment, the present invention further contemplates a kit comprising (a) first container comprising a pharmaceutical composition of a small organic compound of Formula I; and (b) instructions for the use thereof for inhibition of PCSK9 protein biological activity.

In one embodiment, the present invention further contemplates a small organic compound of Formula I for use in treating hypercholesterolemia. In one embodiment, the present invention further contemplates a small organic compound of Formula I for use in lowering serum LDL levels.

In one embodiment, the present invention further contemplates a method for reducing LDL levels in a mammal comprising administering a pharmaceutical composition of a small organic compound of Formula I to the mammal. In one embodiment, the present invention further contemplates a method for reducing LDL levels in a patient comprising administering a pharmaceutical composition of a small organic compound of Formula I to the patient.

In one embodiment, the present invention further contemplates a method for treating hypercholesterolemia in a mammal comprising administering a pharmaceutical composition of a small organic compound of Formula I to the mammal. In one embodiment, the present invention further contemplates a method for treating hypercholesterolemia in a patient comprising administering a pharmaceutical composition of a small organic compound of Formula I to the patient.

In one embodiment, the present invention further contemplates a method for reducing cholesterol levels in a patient in need thereof, wherein said method comprises identifying a patient with elevated serum cholesterol levels, and administering a pharmaceutical composition of a small organic compound of Formula I to the patient. In one embodiment, the present invention further contemplates a method for reducing LDL levels in a patient in need thereof, wherein said method comprises identifying a patient with elevated serum LDL levels, and administering a pharmaceutical composition of a small organic compound of Formula I to the patient. In one embodiment, the present invention further contemplates a method for treating hypercholesterolemia in a patient in need thereof, wherein said method comprises identifying a patient with elevated serum LDL levels, and administering a pharmaceutical composition of a small organic compound of Formula I to the patient.

Definitions

The following abbreviations are used throughout the specification:
Bn: benzyl
Bz: benzoyl
Ac: acetyl
Boc: tert-butoxycarbonyl
Fmoc: 9-fluorenylmethoxycarbonyl
Cbz: benzyloxycarbonyl
TFA: trifluoroacetic acid
NMP: N-methylpyrrolidone
PyBOP: (benzotriazol-1-yloxy)tripyrrolidinophosphoniumhexafluorophosphate
NMM: N-methyl morpholine
HPLC: high pressure liquid chromatography
THF: tetrahydrofuran
DMSO: dimethylsulfoxide
DMF: N,N-dimethylformamide
TMS-Br: trimethylsilyl bromide
Tf: trifluoromethylsulfonyl
HATU: 2-(7-aza-1H-benzotriazole-1-yl)-1,1,3,3-tetramethyluroniumhexafluorophosphate
DIPEA: diisopropylethylamine
DCM: dichloromethane The terms "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN(alkyl)$_2$), trialkyl amines (i.e., N(alkyl)$_3$), substituted alkyl amines (i.e., $NH_2$(substituted alkyl)), di(substituted alkyl) amines (i.e., HN(substituted alkyl)$_2$), tri(substituted alkyl) amines (i.e., N(substituted alkyl)$_3$), alkenyl amines (i.e., $NH_2$(alkenyl)), dialkenyl amines (i.e., HN(alkenyl)$_2$), trialkenyl amines (i.e., N(alkenyl)$_3$), substituted alkenyl amines (i.e., $NH_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

The term "hydrate" refers to the complex formed by the combining of a compound of Formula I and water.

The term "solvate" refers to an association or complex of one or more solvent molecules and a compound of the disclosure. Examples of solvents that form solvates include, but are not limited to, water, isopropanol, ethanol, methanol, dimethylsulfoxide, ethylacetate, acetic acid, and ethanolamine.

The term "small molecule compound" as used herein, refers to an exogenously synthesized organic chemical compound of less than 1,000 Da.

The term "small molecule ligand" as used herein, refers to a small molecule compound that is bound by another naturally occurring biomolecule to form a complex.

The term "small organic compound" as used herein, refers to a small molecule compound, and is synonymous with "organic compound" and "small molecule".

The term "small organic compound ligand" as used herein refers to a small organic compound that is bound by another naturally occurring biomolecule to form a complex.

The term "conformation" as used herein, refers to a three-dimensional stereochemical configuration of any compound and/or molecule. For example, any specific conformation results from a thermodynamic balance between steric interactions, hydrophobic interactions, hydrogen bonding, electrochemical bonding and/or salt bridge interactions in a protein.

The term "LDL-R" and "LDLR" as used herein, refers to an abbreviation for the low density lipoprotein receptor. The abbreviation may be in reference to the entire LDL-R receptor protein or any portion thereof. LDL-Rs reside on a cell surface and can bind to low density lipoproteins such that the LDL-R/LDL complex become internalized within a cell (i.e., for example, a hepatocyte), wherein the LDL is released and the LDL-R is recycled back to the cell surface.

The term, "binding interface" as used herein, refers to any collection of attractive interactions (i.e., for example, hydrogen bonding, electrostatic interactions, hydrophobic interactions, etc) between the functional groups (i.e., for example, hydroxyl, amide, amine, carboxyl, amidine, guanidine, hydrocarbon, sulfonyl etc.) of at least two different molecules.

The collection of attractive forces forms a stable molecular plane thereby forming a 'binding interface' between the at least two molecules.

The term "induced fit" as used herein, refers to any acceptance of a small molecule compound requiring a change in the receiving molecule's conformation. Such a conformation may be facilitated by a translational/rotational movement of amino acid side chains and flexible loops, thereby rearranging the electrostatic and/or hydrophobic fields.

The term "complex" or "composition" as used herein, refers to any chemical association of two or more ions or molecules joined usually by weak electrostatic bonds rather than by covalent bonds. For example, a complex or composition may be formed between a small molecule compound as described herein and a PCSK9 amino acid sequence, thereby creating a small molecule compound: PCSK9 amino acid sequence complex or composition. Optionally, such complexes or compositions may also include, but are not limited to, an LDLR amino acid sequence or any portion thereof, including but not limited to the EGFA region.

The term "hydrogen bond" as used herein, an electrostatic attraction between a hydrogen atom in one polar molecule (as of water) and a small electronegative atom (as of oxygen, nitrogen, or fluorine) in usually another molecule of the same or a different polar substance.

The term "salt bridge" as used herein, refers to any interaction or a combinations of interactions, such as hydrogen bonding and/or electrostatic interactions, which align cationic and anionic chemical structures in such a way that the charged moieties overlap.

The term "interaction" as used herein, refers to any effect that one molecule and/or functional group may have on another molecule and/or functional group. Such effects may include, but are not limited to, steric (i.e., for example, physical), electrostatic (i.e., for example, electrical attraction or repulsion), electromagnetic, hydrophilic, or hydrophobic effects.

The term "overlap" as used herein, refers to any positioning of molecules in such a way that the electronic structure of one molecule is on top of, and extending past the border of another molecule, or be positioned in this way.

The term "hypercholesterolemia" as used herein, refers to any medical condition wherein blood cholesterol levels are elevated above the clinically recommended levels. For example, if cholesterol is measured using low density lipoproteins (LDLs), hypercholesterolemia may exist if the measured LDL levels are above, for example, approximately 75 mg/dl. Alternatively, if cholesterol is measured using free plasma cholesterol, hypercholesterolemia may exist if the measured free cholesterol levels are above, for example, approximately 200-220 mg/dl.

The term "hypocholesterolemia" as used herein, refers to any medical condition wherein blood cholesterol levels are below clinically recommended levels. For example, if total cholesterol or LDL-C levels are measured as below the $5^{th}$ percentile of the general population after adjustment for gender, race, and age.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "disease" and/or "disorder", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors The term "affinity" as used herein, refers to the measure of the thermodynamic tendency of two or more molecules to assemble to form a multi-part complex and to remain assembled in said complex. For example, a small molecule ligand has a high affinity for PCSK9 and is thermodynamically favored to form a complex. It is understood that a change in conditions (e.g., pH during the receptor internalization process) may reduce the affinity of the molecules such that they dissociate, or separate, from one another. For example, pH changes can result in a decrease in the LDL affinity for LDLR and subsequent dissociation of that complex.

The term "derived from" as used herein, refers to the source of a compound. In one respect, a compound may be derived from an organism or particular species. In another respect, a compound may be derived from a larger complex. In another respect, a compound may be derived by chemical modification of part or all of a larger complex.

The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur. and forming a contiguous protein backbone. In general, a protein comprises amino acids having an order of magnitude within the hundreds.

The term "peptide" as used herein, refers to any of various amides that are derived from three or more amino acids by combination of the amino group of one acid with the carboxyl group of another and are usually obtained by partial hydrolysis of proteins. In general, a peptide comprises amino acids having an order of magnitude within the tens or smaller.

The term, "purified" or "isolated", as used herein, may refer to a composition that has been subjected to treatment (i.e., for example, fractionation) to remove various other components, and which composition substantially retains its expressed biological activity.

As used herein, the term "substantially purified" refers to molecules, such as small molecule compound, that are removed from their normal environment, isolated or separated, and are at least 60% free, preferably 75% free, and more preferably 90% free from other components with which they are normally associated.

The term "purified to homogeneity" is used to include compositions that have been purified to "apparent homogeneity" such that there is single small molecule compound species (i.e., for example, based upon SDS-PAGE or HPLC analysis). A purified composition is not intended to mean that all trace impurities have been removed.

The term "biocompatible", as used herein, refers to any material does not elicit a substantial detrimental response in the host. There is always concern, when a foreign object is introduced into a living body, that the object will induce an immune reaction, such as an inflammatory response that will have negative effects on the host. In the context of this invention, biocompatibility is evaluated according to the application for which it was designed: for example; a bandage is regarded a biocompatible with the skin, whereas an implanted medical device is regarded as biocompatible with the internal tissues of the body. Preferably, biocompatible materials include, but are not limited to, biodegradable and biostable materials.

The terms "amino acid sequence" and "polypeptide sequence" as used herein, are interchangeable and to refer to a contiguous sequence of multiple amino acids.

The term "derivative" as used herein, refers to any chemical modification of a small molecule compound. Examples of such modifications would include, but are not limited to, replacement of a hydrogen by an alkyl, aryl, hydroxyl, sulfhydryl, sulfoxyl, sulfonyl, acyl, phosphoryl, alkoxyl, amino or amino heterocyclic group. Other possible chemical modification might include, but are not limited to, C-terminal amides, and acyl or sulfonyl N-terminal modifications.

The term "bind" as used herein, includes any physical attachment or close association, which may be permanent or temporary. Generally, an interaction of hydrogen bonding, hydrophobic forces, van der Waals forces, covalent and ionic bonding etc., facilitates physical attachment between the molecule of interest and the analyte/target being measuring/affected. The "binding" interaction may be brief as in the situation where binding causes a chemical reaction to occur. That is typical when the binding component is an enzyme and the analyte/target is a substrate for the enzyme. Reactions resulting from contact between the binding agent and the analyte/target are also within the definition of binding for the purposes of the present invention.

Chemical Terminology:
Alkyl: a chain consisting of only carbon and hydrogen atoms such that each carbon atom directly connects to exactly 4 different atoms, using only single bonds.

Lower alkyl: an alkyl chain containing 1-6 carbon atoms.
Branched alkyl: an alkyl chain containing one or more carbon atoms which are directly connected to more than 2 other carbon atoms without creating a ring of carbon atoms.
Hydroxyalkyl: an alkyl chain where at least one carbon atom is bonded to a hydroxyl, that is, —OH.
Cycloalkyl: an alkyl chain forming a ring. Examples would include cyclopropyl or -cyclohexyl.
Heterocycle: a chain of atoms forming a ring and containing one or more "heteroatoms"; that is, atoms other than C or H able to form stable covalent bonds, such as N, O, or S. In this context, "heterocyle" will imply a non-aromatic ring. Examples include a tetrahydrofuran ring, with 4 carbon atoms and one oxygen, or a morpholine, with 4 carbon atoms and one nitrogen and one oxygen arranged such that the N and O are 1,4 to one another.
Aromatic ring: a ring of atoms containing alternating single and double "pi" bonds such that the number pi electrons (typically 2 per double bonds for stable compounds) is an even number but not a multiple of four.
Acyl: a carbonyl containing radical: —CO—R. In this document, R=affords a typical peptide modifying group, such as: —$CH_3$ (acetyl), —CH(CH2)$_2$ (isobutyryl).
Benzoyl: a carbonyl containing radical: —CO-Ph, where Ph=phenyl.
Sulfonyl: a sulfonyl containing radical: —$SO_2$—R.
Carbamoyl: a radical: —$CONR_1R_2$
Alkoxy: an alkyl chain containing one or more ether (—O—) linkages, such as: —$CH_2CH_2OCH_3$.
Aryl: phenyl or substituted phenyl
Heteroaryl: a 5 or 6 membered aromatic heterocycle
Fused heterocyle: a ring system, such as indole, containing two or more fused rings, of which at least one is a heterocycle. The rings need not be aromatic: indoline has an aromatic ring fused to a non-aromatic ring.
Negatively charged polar group: A polar group carrying a negative charge at physiologic pH.

DETAILED DESCRIPTION OF THE INVENTION

Figure 1:
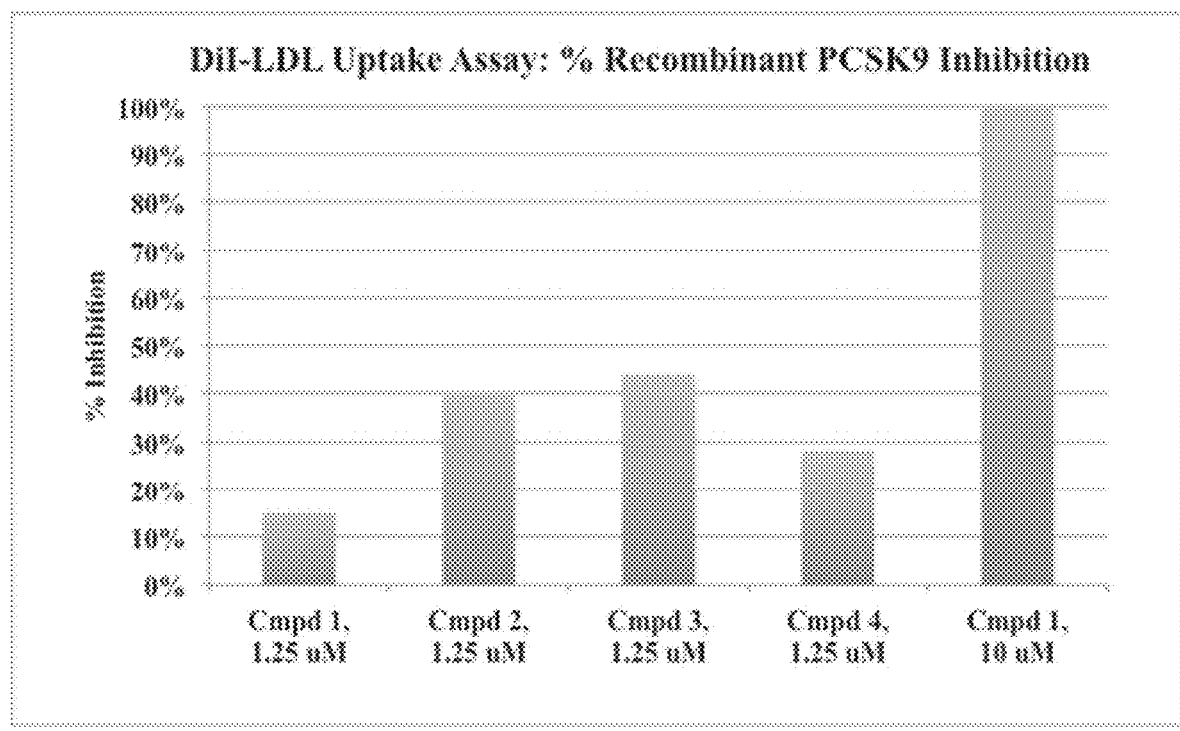
FIG. 1 shows exemplary data of % PCSK9 modulation in HepG2 cells in a DiI-LDL Uptake Assay. The cells were incubated in a 96-well plate for a total of 16h in the absence or presence of recombinant PCSK9 (final concentration 2.5 ug/ml) protein alone or recombinant PCSK9 protein pre-mixed with indicated concentration of experimental compounds (Cmpd #). After 16h, DiI-LDL (final concentration 5 ug/ml) was added to the incubation mixtures. After 4h, cells are stained with Hoechst 33342 for 30 minutes, then rinsed with phosphate buffered saline, and then a final volume of 100 ul phosphate buffered saline was added to each well. The fluorescence was measured (DiI: excitation at 550 nm and emission at 590 nm; Hoechst: excitation at 355 nm, emission at 460 nm). The percent recombinant PCSK9 inhibition was calculated as ['Compound Dose DiI Fluorescence'-'2.5 ug/ml PCSK9-treated DiI Fluorescence']/['No PCSK9 DiI Fluorescence'-'2.5 ug/ml PCSK9-treated DiI Fluorescence']×100%.
Figure 2:
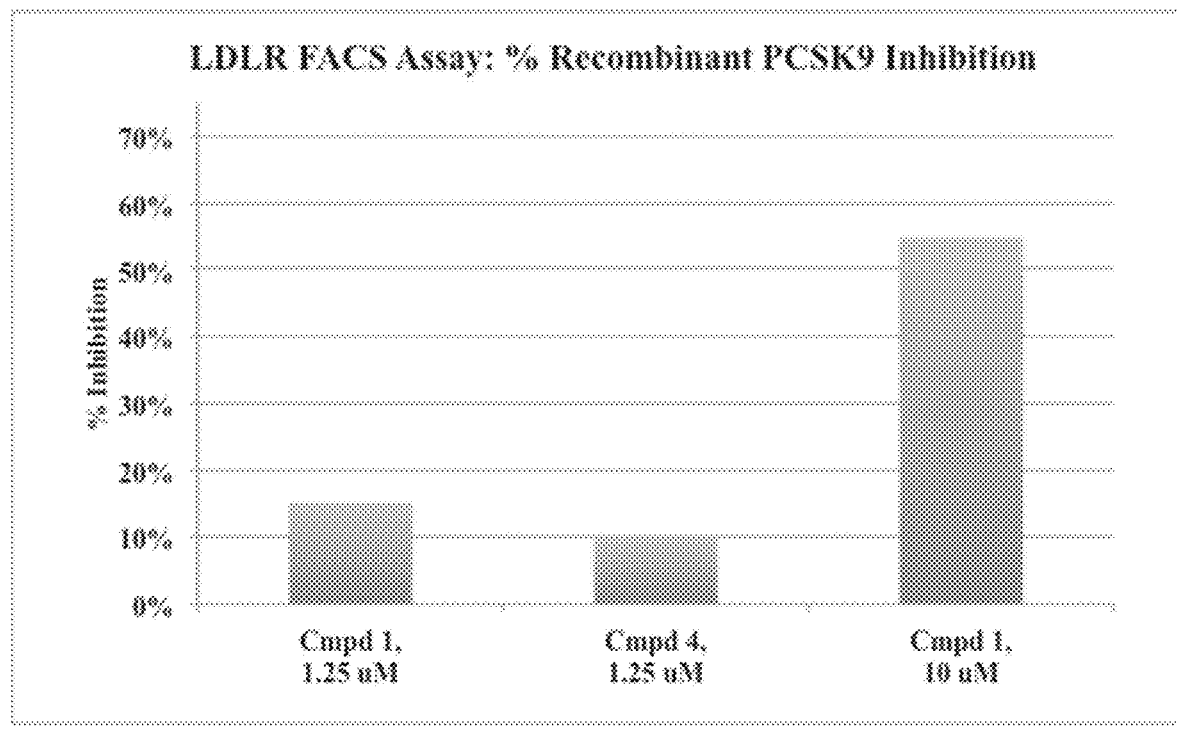
FIG. 2 shows exemplary data of % PCSK9 inhibition in HuH7 cells in an LDLR FACS Assay. The cells were incubated in 24-well plates for a total of 6h in the absence or presence of recombinant PCSK9 protein (final concentration of 5.0 ug/ml), or in the presence of PCSK9 protein mixed with indicated concentration of experimental compound (Cmpd #). After 6 hours, the cells were released from the plate, stained with anti-LDLR antibody, then rinsed, counterstained with DAPI, and then measured by fluorescence activated cell sorting (FACS). The percent recombinant PCSK9 inhibition was calculated as ['Compound Dose LDLR Fluorescence'-'5.0 ug/ml PCSK9-treated LDLR Fluorescence']/['No PCSK9 Basal LDLR Fluorescence'-'5.0 ug/ml PCSK9-treated LDLR Fluorescence']×100%.

This invention is related to the field of PCSK9 biology and use of compounds for treatment including conditions of hypercholesterolemia and hypocholesterolemia. In particular, the invention provides compositions of ligands that bind and alter PCSK9 biological conformation and activity. These ligands are small molecule chemical compounds, and more preferably small molecule compounds less than 800 Da. Altering the conformation of PCSK9 can change the interactions between PCSK9 and an endogenous low density lipoprotein receptor, and can lead to reduced or increased levels of circulating LDL-cholesterol. High LDL-cholesterol levels are associated with increased risk for heart disease. Low LDL-cholesterol levels may be problematic in other conditions, such as liver dysfunction; thus, there is also utility for ligands that can raise LDL levels.

I. Physiological Role of Native PCSK9

Proprotein convertase subtilisin/kexin type 9, also known as PCSK9, is an enzyme that in humans is encoded by the PCSK9 gene. Seidah et al., "The secretory proprotein convertase neural apoptosis-regulated convertase 1 (NARC-1): liver regeneration and neuronal differentiation" *Proc. Natl. Acad. Sci. U.S.A.* 100 (3): 928-933 (2003). Similar genes (orthologs) are found across many species. Many enzymes, including PSCK9, are inactive when they are first synthesized, because they have a section of peptide chains that blocks their activity; proprotein convertases remove that section to activate the enzyme.

The PSCK9 gene encodes a proprotein convertase belonging to the proteinase K subfamily of the secretory subtilase family. The encoded protein is synthesized as a soluble zymogen that undergoes autocatalytic intramolecular processing in the endoplasmic reticulum. The protein may function as a proprotein convertase. For example, a human PCSK9 amino acid sequence is:

001 mgtvssrrsw wplplllll lllgpagara qededgdyee lvlalrseed glaeapehgt 061 tatfhrcakd pwrlpgtyvv vlkeethlsq sertarrlqa qaarrgyltk ilhvfhgllp 121 gflvkmsgdl lelalklphv dyieedssvf aqsipwnler itppryrade yqppdggsly 181 evylldtsiq sdhreiegrv mvtdfenvpe edgtrfhrqa skcdshgthl agvvsgrdag 241 vakgasmrsl rvlncqgkgt vsgtliglef irksqlvqpv gplvvllpla ggysrvlnaa 301 cqrlaragvv lvtaagnfrd daclyspasa pevitvgatn aqdqpvtlgt lgtnfgrcvd 361 lfapgediig assdcstcfv sqsgtsqaaa hvagiaamml saepeltlae lrqrlihfsa 421 kdvineawfp edqrvltpnl vaalppsthg agwqlfcrtv wsahsgptrm atavarcapd 481 eellscssfs rsgkrrgerm eaqggklvcr ahnafggegv yaiarcllp qancsvhtap 541 paeasmgtrv hchqqghvlt gcsshweved lgthkppvlr prgqpnqcvg hreasihasc 601 chapgleckv kehgipapqe qvtvaceegw tltgcsalpg tshvl-
gayav dntcvvrsrd
661 vsttgstseg avtavaiccr srhlaqasqe lq (Accession No.
NP_777596) (SEQ ID NO:1).

PSCK9 is believed to play a regulatory role in cholesterol homeostasis. For example, PCSK9 can bind to the epidermal growth factor-like repeat A (EGF-A) domain of the low-density lipoprotein receptor (LDL-R) resulting in LDL-R internalization and degradation. Clearly, it would be expected that reduced LDL-R levels result in decreased metabolism of LDL-C, which could lead to hypercholesterolemia.

As it is estimated that approximately 9 million Americans have a high or very high risk for heart-related problems that could benefit from PCSK9 inhibitors (especially when in combination with statins). PCSK9 inhibitors could result in such widespread usage having the potential to replace statins in certain conditions. PCSK9 has medical significance because it acts in cholesterol homeostasis. Drugs that block PCSK9 biological actions are believed to lower circulating low-density lipoprotein cholesterol (LDL-C) levels (i.e., for example, by increasing the availability of LDL-Rs and, consequently, LDL-C clearance). Such drugs are beginning Phase III clinical trials to assess their safety and efficacy in humans, and to determine if they can improve outcomes in heart disease.

Drugs that inhibit LDL-R/PCSK9 complex formation have been suggested to lower cholesterol much more than conventionally available cholesterol-lowering drugs (i.e., for example, statins). It is biologically plausible that this would also lower heart attacks and other diseases caused by raised cholesterol. Studies with humans, including phase III clinical trials now underway, are focused as to whether PCSK9 inhibition actually does lower cardiovascular disease, with acceptable side effects. Lopez D., "Inhibition of PCSK9 as a novel strategy for the treatment of hypercholesterolemia" *Drug News Perspect.* 21(6): 323-e30 (2008); Steinberg et al., "Inhibition of PCSK9: a powerful weapon for achieving ideal LDL cholesterol levels" *Proc. Natl. Acad. Sci. U.S.A.* 106(24): 9546-9547 (2009); Mayer, "Annexin A2 is a C-terminal PCSK9-binding protein that regulates endogenous low density lipoprotein receptor levels" *J. Biol. Chem.* 283(46): 31791-31801 ((2008); and Anonomyous, "Bristol-Myers Squibb selects Isis drug targeting PCSK9 as development candidate for prevention and treatment of cardiovascular disease" *Press Release. Fierre-Biotech.* 2008 Apr. 8.

Currently, it has been reported that PCSK9 antibody drugs are in clinical trials (e.g., for example, Sanofi/Regeneron, Amgen, Pfizer, Novartis, Roche). However, one disadvantage of antibody therapy is that the administration is performed by subcutaneous or intravenous injection. A number of monoclonal antibodies that bind to PCSK9 near the catalytic domain that interact with the LDL-R and hence inhibit LDL-R/PCSK9 complex formation are currently in clinical trials. These antibodies include AMG145 (Amgen), 1D05-IgG2 (Merck & Co.), and SAR236553/REGN727 (Aventis/Regeneron). Lambert et al., "The PCSK9 decade" *J. Lipid Res.* 53(12): 2515-2524 (2012).

Peptides that mimic the EGF-A domain of the LDL-R have been developed to inhibit LDL-R/PCSK9 complex formation. Shan et al., "PCSK9 binds to multiple receptors and can be functionally inhibited by an EGF-A peptide". *Biochem. Biophys. Res. Commun.* 375(1): 69-73 (2008). Peptidic PCSK9 inhibitors of the EGF-B binding site were identified by screening both linear and disulfide-constrained phage-displayed peptide libraries. This approach identified a 13-amino acid peptide (Pep2-8) that includes structural mimicry of the natural binding domain of LDL receptor. The peptide inhibitor binding site was determined to largely overlap with that of the EGF(A) domain; therefore, Pep2-8 acts a competitive inhibitor of LDL receptor binding. This is akin to the inhibition mechanism of anti-PCSK9 monoclonal antibodies, which also disrupt the interaction of the LDL receptor-EGF(A) domain with PCSK9. Zhang et al., "Identification of a Small Peptide That Inhibits PCSK9 Protein Binding to the Low Density Lipoprotein Receptor" *J Biol Chem* 289:942-955 (2014).

PCSK9 antisense oligonucleotides (Isis Pharmaceuticals) have been shown to increase expression of the LDL-R and decrease circulating total cholesterol levels in mice. Graham et al., "Antisense inhibition of proprotein convertase subtilisin/kexin type 9 reduces serum LDL in hyperlipidemic mice" *J. Lipid Res.* 48(4): 763-767 (2007). It has also been reported that a locked nucleic acid (Santaris Pharma) reduced PCSK9 mRNA levels in mice. Gupta et al., "A locked nucleic acid antisense oligonucleotide (LNA) silences PCSK9 and enhances LDLR expression in vitro and in vivo" *PLoS ONE* 5(5): e10682 (2010); and Lindholm et al., "PCSK9 LNA antisense oligonucleotides induce sustained reduction of LDL cholesterol in nonhuman primates". *Mol. Ther.* 20(2):376-381 (2012). Initial clinical trials of an RNAi (ALN-PCS, Alnylam Pharmaceuticals) has shown positive results as an effective means of inhibiting LDL-R/PCSK9 complex formation. Frank-Kamenetsky et al., "Therapeutic RNAi targeting PCSK9 acutely lowers plasma cholesterol in rodents and LDL cholesterol in nonhuman primates" *Proc. Natl. Acad. Sci. U.S.A.* 105(33): 11915-11920 (2008).

II. PCSK9 Allosteric Site Modulation Small Molecule Compounds

Variants of PCSK9 can reduce or increase circulating cholesterol. Abifadel et al., "Mutations in PCSK9 cause autosomal dominant hypercholesterolemia" *Nat. Genet.* 34 (2): 154-156 (2003). LDL-C is normally removed from the blood when it binds to an LDL-R on the surface of liver cells, and is internalized within the hepatocyte as a receptor-ligand complex. However, when PCSK9 binds to an LDL-R, the LDL-R is concomitantly degraded along with the complexed LDL particle. However, if a PCSK9 is not bound to an LDL-R, the LDL-R is recycled after internalization thereby returning to the surface of the cell for removal of more cholesterol.

In some embodiments, the invention relates to small organic compounds having a modulation effect on PCSK9's ability to form an LDL-R/PCSK9 complex. In some embodiments, the present invention contemplates the use of small organic compounds that bind to a PCSK9 protein and modulate the protein's biological activity. In some embodiments, the small molecules decrease LDL-R/PCSK9 complex formation and are thereby useful to treat various diseases comprising lipid dysregulation. In some embodiments, the small molecules increase LDL-R/PCSK9 complex formation and are thereby useful in research and development of therapies relevant to LDL dysregulation.

Although it is not necessary to understand the mechanism of an invention, it is believed that "gain-of-function" (GOF) PCSK9 mutants may result in conditions including, but not limited to, hypercholesterolemia. For example, compounds that bind to a PCSK9 and increase the affinity of PCSK9's low density lipoprotein receptor for a low density lipoprotein receptor on the surface of a cell (e.g., a hepatocyte) would be expected to increase the symptoms of hypercholesterolemia by increasing low density lipoprotein receptor internalization and degradation.

Although it is not necessary to understand the mechanism of an invention, it is believed that "loss-of-function" (LOF) PCSK9 mutants may result in conditions comprising reduced low density lipoproteins and would be expected to result in hypocholesterolemia thereby reducing the risk of cardiovascular diseases, including but not limited to, coronary heart disease. For example, small molecule compounds that bind to a PCSK9 that decrease the affinity of PCSK9's low density lipoprotein receptor binding site for a low density lipoprotein receptor on the surface of a cell (e.g., a hepatocyte) would be expected to reduce the symptoms of hypercholesterolemia by promoting low density lipoprotein internalization and clearance due to concomitant recycling of the low density lipoprotein receptor.

The presently disclosed embodiments of PCSK9 binding small organic compounds have several advantages over current peptides and ligands described in the art. For example, small molecule PCSK9 binding compounds, as contemplated herein, have the advantage that these compounds are smaller than many previously described peptides. It is envisioned that these small organic compounds can be administered orally without immunological reactions seen with antibody administration, or systemic degradation problems as seen with nucleic acid administration (i.e., antisense or locked nucleic acids). Nonetheless, as these small organic compounds have long half-lives, encapsulation drug delivery systems, such as liposomes or other biodegradable protective compositions, will lengthen these half-lives to a greater extent than either antibodies or nucleic acids. These small organic compounds described in this application are designed de novo to have desirable characteristics, such as for drug-like properties. Although it is not necessary to understand the mechanism of an invention, it is believed that these compounds are also structurally distinct from any previously described PCSK9 modulating small molecules and are reasonably expected to have different physicochemical properties from other PCSK9 binding compounds.

III. Clinical Therapeutics

In some embodiments, the present invention contemplates the administration of a small molecule PCSK9 allosteric inhibitor compound to a subject having a symptom of a cardiovascular disease. In one embodiment, the cardiovascular disease comprises hypercholesterolemia. In one embodiment, the cardiovascular disease comprises hypertension. In one embodiment, the hypercholesterolemia comprises elevated low density lipoprotein levels.

In some embodiments, the present invention contemplates the administration of a small molecule PCSK9 allosteric inhibitor compound to a subject having a symptom of a metabolic disease. In one embodiment, the metabolic disease comprises diabetes.

Although it is not necessary to understand the mechanism of an invention, it is believed that the administration of a PCSK9 allosteric inhibitor small molecule compound (i.e., such as those described herein) induces a conformational shift of the PCSK9 protein such that the affinity of the low density lipoprotein binding site for a low density lipoprotein receptor is decreased, wherein PCSK9/LDL-R complex formation is decreased. The decrease in PCSK9/LDL-R complex formation results in an increase in the bioavailability of LDL-R receptors for binding to circulating LDL, thereby increasing the internalization and clearance of LDL by LDL-R. It is further believed that a small molecule PCSK9 allosteric inhibitor compound may result in increased bioavailability of hepatocyte cell LDL-Rs.

Further, although it is not necessary to understand the mechanism of an invention, it is believed that the administration of a PCSK9 allosteric activator small molecule compound (i.e., such as those described herein) induces a conformational shift of the PCSK9 protein such that the affinity of the low density lipoprotein binding site for a low density lipoprotein receptor is increased, wherein PCSK9/LDL-R complex formation is increased or stabilized. The increase or stabilization in PCSK9/LDL-R complex formation results in a decrease in the bioavailability of LDL-R receptors for binding to circulating LDL, thereby decreasing the internalization and clearance of LDL by LDL-R. It is further believed that a PCSK9 allosteric activator compound may result in decreased bioavailability of hepatocyte cell LDL-Rs.

A. Hypercholesterolemia

Hypercholesterolemia (also spelled hypercholesterolaemia) is the presence of high levels of cholesterol in the blood. It is a form of "hyperlipidemia" (elevated levels of lipids in the blood) and "hyperlipoproteinemia" (elevated levels of lipoproteins in the blood). Durrington, P "Dyslipidaemia" *The Lancet* 362(9385):717-731. Hypercholesterolemia is typically due to a combination of environmental and genetic factors. Environmental factors include obesity and dietary choices. Genetic contributions are usually due to the additive effects of multiple genes, though occasionally may be due to a single gene defect such as in the case of familial hypercholesterolaemia. A number of secondary causes exist including: diabetes mellitus type 2, obesity, alcohol, monoclonal gammopathy, dialysis, nephrotic syndrome, obstructive jaundice, hypothyroidism, Cushing's syndrome, anorexia nervosa, medications (thiazide diuretics, ciclosporin, glucocorticoids, beta blockers, retinoic acid). Bhatnagar et al., (2008) "Hypercholesterolaemia and its management" *BMJ* 337: a993. Genetic abnormalities are in some cases completely responsible for hypercholesterolemia, such as in familial hypercholesterolemia where there is one or more genetic mutations in the autosomal dominant APOB gene, the autosomal recessive LDLRAP1 gene, autosomal dominant familial hypercholesterolemia (HCHOLA3) variant of the PCSK9 gene, or the LDL receptor gene. "Hypercholesterolemia" *Genetics Home Reference* U.S. National Institutes of Health, ghr.nlm.nih.gov/condition=hypercholesterolemia. Even when there is no single mutation responsible for hypercholesterolemia, genetic predisposition still plays a major role in combination with sedentary lifestyle, obesity, or an atherogenic diet. Citkowitz et al., (2010) "Polygenic Hypercholesterolemia". *eMedicine Medscape*, emedicine.medscape.com/article/121424-overview.

Cholesterol is a sterol. It is one of three major classes of lipids which all animal cells utilize to construct their membranes and is thus manufactured by all animal cells. Plant cells do not manufacture cholesterol. It is also the precursor of the steroid hormones, bile acids and vitamin D. Since cholesterol is insoluble in water, it is transported in the blood plasma within protein particles (lipoproteins). Lipoproteins are classified by their density: very low density lipoprotein (VLDL), intermediate density lipoprotein (IDL), low density lipoprotein (LDL) and high density lipoprotein (HDL). Biggerstaff et al., (2004). "Understanding lipoproteins as transporters of cholesterol and other lipids" *Adv Physiol Educ* 28 (1-4): 105-6. All the lipoproteins carry cholesterol, but elevated levels of the lipoproteins other than HDL (termed non-HDL cholesterol), particularly LDL-cholesterol are associated with an increased risk of atherosclerosis and coronary heart disease. Carmena et al., (2004) "Atherogenic lipoprotein particles in atherosclerosis" *Circulation* 109(23 Suppl 1): III 2-7. In contrast, higher levels of HDL cholesterol are protective. Kontush et al., (2006) "Antiatherogenic small, dense HDL—guardian angel of the arterial wall?" *Nat Clin Pract Cardiovasc Med* 3(3):144-153. Elevated levels of non-HDL cholesterol and LDL in the blood may be a consequence of diet, obesity, inherited (genetic) diseases (such as LDL receptor mutations in familial hypercholesterolemia), or the presence of other diseases such as diabetes and an underactive thyroid. Total cholesterol is the amount of all of the fats in your blood. These fats are called lipids. There are different types of lipid that make up your total cholesterol. The two most important types are: low density lipoprotein (LDL)—"bad" cholesterol and high density lipoprotein (HDL)—"good" cholesterol. High cholesterol, especially "bad" cholesterol (LDL), can clog your arteries. This may reduce blood flow to your heart. It can lead to heart disease, stroke, or heart attack. Cholesterol is measured in milligrams per deciliter (mg/dL). In conditions such as heart disease or diabetes, LDL cholesterol should stay below 100 mg/dL. If there is a risk for heart disease, LDL cholesterol should be lower than 130 mg/dL. In general, LDL cholesterol should be lower than 160-190 mg/dL. Alternative, HDL "good" cholesterol should be high. For example, HDL levels in men should be above 40 mg/dL, while HDL levels should be above 50 mg/dL for women.

One symptom of hypercholesterolemia comprises a long-standing elevation of serum cholesterol that can lead to atherosclerosis. Bhatnagar et al., (2008) "Hypercholesterolaemia and its management" *BMJ* 337: a993. Over a period of decades, chronically elevated serum cholesterol contributes to formation of atheromatous plaques in the arteries. This can lead to progressive stenosis (narrowing) or even complete occlusion (blockage) of the involved arteries. Alternatively smaller plaques may rupture and cause a clot to form and obstruct blood flow. Finn A V, Nakano M, Narula J, Kolodgie F D, Virmani R (July 2010). "Concept of vulnerable/unstable plaque" *Arterioscler. Thromb. Vasc. Biol.* 30(7): 1282-1292. A sudden occlusion of a coronary artery results in a myocardial infarction or heart attack. An occlusion of an artery supplying the brain can cause a stroke. If the development of the stenosis or occlusion is gradual blood supply to the tissues and organs slowly diminishes until organ function becomes impaired. At this point that tissue ischemia (restriction in blood supply) may manifest as specific symptoms including, but not limited to, temporary ischemia of the brain (commonly referred to as a transient ischemic attack) may manifest as temporary loss of vision, dizziness and impairment of balance, aphasia (difficulty speaking), paresis (weakness) and paresthesia (numbness or tingling), usually on one side of the body. Insufficient blood supply to the heart may manifest as chest pain, and ischemia of the eye may manifest as transient visual loss in one eye. Insufficient blood supply to the legs may manifest as calf pain when walking, while in the intestines it may present as abdominal pain after eating a meal. Grundy et al., (1998) "Primary prevention of coronary heart disease: guidance from Framingham: a statement for healthcare professionals from the AHA Task Force on Risk Reduction. American Heart Association" *Circulation* 97(18):1876-1887.

B. Hypocholesterolemia

Hypocholesterolemia is the presence of abnormally low (hypo-) levels of cholesterol in the blood (-emia). Although the presence of high total cholesterol (hyper-cholesterolemia) correlates with cardiovascular disease, a defect in the body's production of cholesterol can lead to adverse consequences as well. Cholesterol is an essential component of mammalian cell membranes and is required to establish proper membrane permeability and fluidity. It is not clear if a lower than average cholesterol level is directly harmful; it is often encountered in particular illnesses.

Possible causes of low cholesterol include, but are not limited to, statins, hyperthyroidism, or an overactive thyroid gland, adrenal insufficiency, liver disease, malabsorption (inadequate absorption of nutrients from the intestines), such as in celiac disease, malnutrition, abetalipoproteinemia (a genetic disease that causes cholesterol readings below 50 mg/dl), hypobetalipoproteinemia (a genetic disease that causes cholesterol readings below 50 mg/dl, manganese deficiency, Smith-Lemli-Opitz syndrome, Marfan syndrome, leukemias and other hematological diseases.

Demographic studies suggest that low cholesterol is associated with increased mortality, mainly due to depression, cancer, hemorrhagic stroke, aortic dissection and respiratory diseases. Jacobs et al., (1992). "Report of the Conference on Low Blood Cholesterol: Mortality Associations" *Circulation* 86 (3): 1046-1060; and Suarez E. C., (1999) "Relations of trait depression and anxiety to low lipid and lipoprotein concentrations in healthy young adult women". *Psychosom Med* 61(3): 273-279. It is also possible that whatever causes the low cholesterol level also causes mortality, and that the low cholesterol is simply a marker of poor health.

C. Diabetes

Diabetes affects more than 20 million Americans. Over 40 million Americans have pre-diabetes (which often develops before type 2 diabetes). Diabetes is usually a lifelong (chronic) disease in which there is a high level of sugar in the blood. Insulin is a hormone produced by the pancreas to control blood sugar. Diabetes can be caused by too little insulin, resistance to insulin, or both. To understand diabetes, it is important to first understand the normal process by which food is broken down and used by the body for energy.

Several things happen when food is digested. A sugar called glucose enters the bloodstream. Glucose is a source of fuel for the body. An organ called the pancreas makes insulin. The role of insulin is to move glucose from the bloodstream into muscle, fat, and liver cells, where it can be used as fuel.

People with diabetes have high blood sugar because their body cannot move sugar into fat, liver, and muscle cells to be stored for energy. This is because either their pancreas does not make enough insulin or their cells do not respond to insulin normally.

There are two major types of diabetes. The causes and risk factors are different for each type. Type 1 diabetes can occur at any age, but it is most often diagnosed in children, teens, or young adults. In this disease, the body makes little or no insulin. Daily injections of insulin are needed. The exact cause is unknown. Type 2 diabetes makes up most diabetes cases. It most often occurs in adulthood. But because of high obesity rates, teens and young adults are now being diagnosed with it. Many people with type 2 diabetes do not know they have it.

Gestational diabetes is high blood sugar that develops at any time during pregnancy in a woman who does not have diabetes.

Diabetes symptoms may result from high blood sugar level and include, but are not limited to, blurry vision, excess thirst, fatigue, hunger, urinating often and weight loss.

IV. Pharmaceutical Compositions

The present invention further provides pharmaceutical compositions (e.g., comprising the compounds described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, (e.g., intrathecal or intraventricular), administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral, sublingual or buccal administration include powders or granules, suspensions or solutions in water or non-aqueous media, capsules, gels, drops, strips, gums, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

In some embodiment, the pharmaceutical compositions may further comprise other drugs and/or hormones. For example, the pharmaceutical composition may further comprise a statin drug. Statins (or HMG-CoA reductase inhibitors) are a class of drugs used to lower cholesterol levels by inhibiting the enzyme HMG-CoA reductase, which plays a role in the production of cholesterol in the liver. Increased cholesterol levels have been associated with cardiovascular diseases, and statins are therefore used in the prevention of these diseases. Lewington et al., "Blood cholesterol and vascular mortality by age, sex, and blood pressure: a meta-analysis of individual data from 61 prospective studies with 55,000 vascular deaths" *Lancet* 370(9602): 1829-1839 (2007). Research has found that statins are most effective for treating cardiovascular disease (CVD) as a secondary prevention strategy, with questionable benefit in those with elevated cholesterol levels but without previous CVD. Taylor et al. "Statins for the primary prevention of cardiovascular disease". In: Taylor, Fiona. Cochrane Database Syst Rev (1) (2011). Statins have rare but severe adverse effects, particularly muscle damage.

Specific examples of statins include, but are not limited to, atorvastatin (Lipitor® and Torvast®), fluvastatin (Lescol®), lovastatin (Mevacor®, Altocor®, Altoprev®), pitavastatin (Livalo®, Pitava®), pravastatin (Pravachol®, Selektine®, Lipostat®), rosuvastatin (Crestor®) and simvastatin (Zocor®, Lipex®). Several combination preparations of a statin and another agent, such as ezetimibe/simvastatin, are also available.

Specific examples of cardiovascular drugs include, but are not limited to, propranolol, *digitalis*, amlodipine besylate, and nifedipine.

Specific examples of other pharmaceutical compositions may further include, but are not limited to, exetimibe (Zetia®), amlodipine besylate (Norvasco), niacin, sitagliptin (Januvia®), metformin or orlistat (Alli®/Xenical®).

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the active pharmaceutical ingredient(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the small molecule compounds described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the small molecule compound is administered in maintenance doses, ranging from 0.01 μg to 100 g per kg of body weight, once or more daily, to once every 20 years.

In one embodiment, the present invention further contemplates a commercial package comprising (a) a pharmaceutical composition comprising a small molecule compound as contemplated herein; and (b) instructions for the use thereof for treatment of hypercholesterolemia. In one embodiment, the present invention further contemplates a commercial package comprising (a) a pharmaceutical composition comprising a small molecule compound as contemplated herein; and (b) instructions for the use thereof for treatment of hypocholesterolemia. In one embodiment, the present invention further contemplates a commercial package comprising (a) a pharmaceutical composition comprising a small molecule compound as contemplated herein; and (b) instructions for the use thereof for inhibition of PCSK9 protein biological activity. In one embodiment, the present invention further contemplates a commercial package comprising (a) a pharmaceutical composition comprising a small molecule compound as contemplated herein; and (b) instructions for the use thereof for increasing the biological activity of PCSK9 protein. In one embodiment, the present invention further contemplates a commercial package as a kit.

In one embodiment, the present invention further contemplates a kit comprising (a) a pharmaceutical composition comprising a small molecule compound as contemplated herein; and (b) instructions for the use thereof for treatment of hypercholesterolemia. In one embodiment, the present invention further contemplates a kit comprising (a) a pharmaceutical composition comprising a small molecule compound as contemplated herein; and (b) instructions for the use thereof for treatment of hypocholesterolemia. In one embodiment, the present invention further contemplates a kit comprising (a) a pharmaceutical composition comprising a small molecule compound as contemplated herein; and (b) instructions for the use thereof for inhibition of PCSK9 protein biological activity. In one embodiment, the present invention further contemplates a kit comprising (a) a pharmaceutical composition comprising a small molecule compound as contemplated herein; and (b) instructions for the use thereof for increasing the biological activity of PCSK9 protein.

V. Description of Chemistry

Phenylalanine Scaffold—Synthesis

Compounds of a phenylalanine scaffold of Formula I may be synthesized from commercial materials, such as a protected 4-bromophenylalanine derivative, which can then be converted to biphenyl-like structures using routine palladium coupling techniques (Scheme 1).

Scheme 1

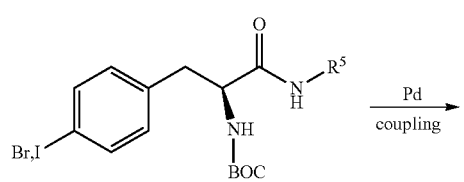

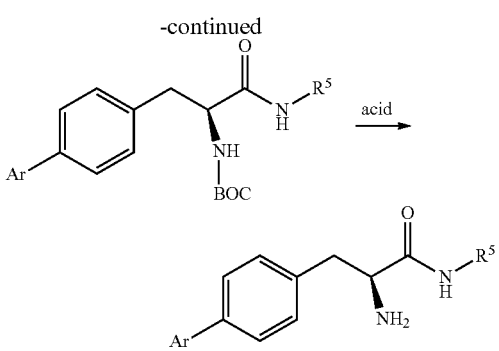

In cases where a commercial peptide starting material is not available, more exotic amino acids may be synthesized by the Strecker method (Scheme 2), using KCN/acid (Strecker, A. Annalen der Chemie und Pharmazie 1850, 75, 27-45.)

Scheme 2

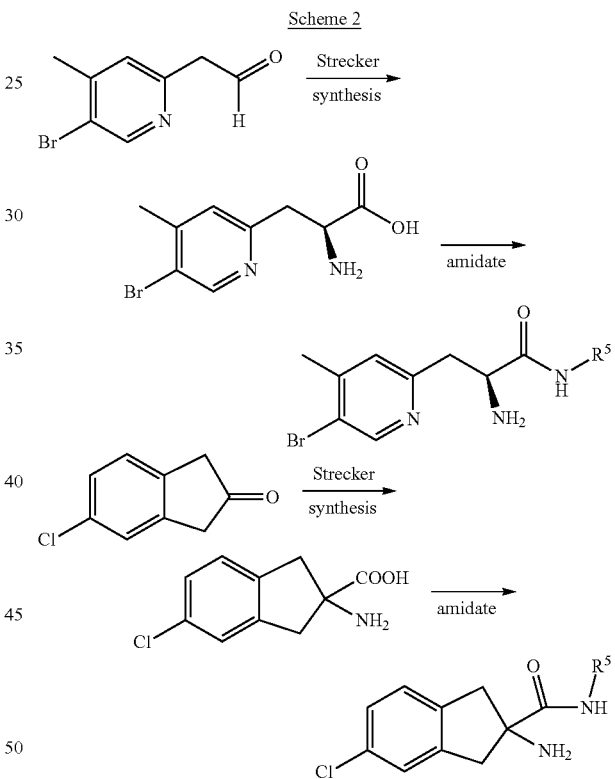

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Compound Synthesis

Compound 1

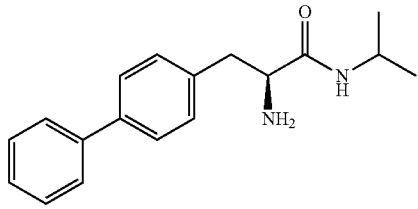 [SMILES: CC(C)NC(=O)[C@@H](N)Cc1ccc(-c2ccccc2)cc1]

Preparation of (S)-3-([1,1'-biphenyl]-4-yl)-2-amino-N-isopropylpropanamide: The title compound was prepared from 4-phenyl-L-phenylalanine using routine peptide chemistry and isolated as the acetate salt. MS calculated for [M] 282.17 and found [M+H]+ 283.09.

Compound 4

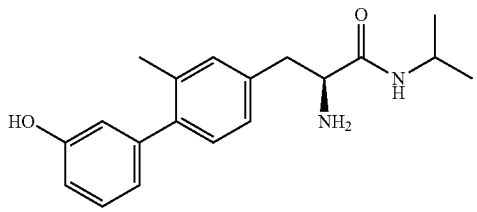 [SMILES: Cc1cc(C[C@H](N)C(=O)NC(C)C)ccc1-c1cccc(O)c1]

STEP-1: Preparation of 4-bromo-3-methylphenyl) methanol: To a stirred solution of LiAlH$_4$ (0.3 g, 8.69 mmol, 2.0 equi) in dry THF (12 mL, 12 vol.) was added ethyl 4-bromo-3-methylbenzoate (1.0 g, 4.344 mol, 1.0 eq.) drop wise on stirring at cold condition under nitrogen atmosphere and continued to stir at RT for 45 min up to completion of the reaction. The reaction mixture was cooled to 0° C. then quenched with saturated Na$_2$SO$_4$ solution and stirred for 5 min, filtered through a pad of celite. The collected filtrate was diluted with water (10 mL) and extracted with EtOAc (3×20 mL). The combined organic layers were dried over anhydrous Na$_2$SO$_4$, filtered and concentrated to obtain compound 1 as a pale yellow oil, which was directly used in the next step without any further purification (850 mg, 70%).

STEP-2: Preparation of 1-bromo-4-(bromomethyl)-2-methylbenzene: To a stirred solution of PPh$_3$(2.1 g, 8.006 mmol, 2.0 eq.) in dry THF (10 mL, 12 vol.) were added bromo benzyl alcohol 1 (0.8 g, 3.980 mol, 1.0 equi) followed by NBS (1.5 g, 8.427 mol, 2.1 eq.) portion wise on stirring for 10 min at 0° C. under nitrogen atmosphere and then stirred for 16 h up to completion of the reaction. The reaction was diluted with water (100 mL) and extracted with EtOAc (3×250 mL). The combined organic layers were washed with saturated NaHCO$_3$ followed by brine solution. Then the organic portion was dried over anhydrous Na$_2$SO$_4$, filtered and concentrated to obtain compound 2 as a brown oil, which was used directly in the next step without any further purification (0.8 g, 76%).

STEP-3: preparation of ethyl 3-(4-bromo-3-methylphenyl)-2-(diphenylmethyleneamino) propanoate: To a stirred solution of compound 3 (14 g, 0.0523 mol, 1.0 eq.) in DMSO (280 mL, 20 vol.) was added KOBu (7.5 g, 0.067 mol, 1.28 eq.) portion wise on stirring for 10 min and continued to stir for 30 min at RT and then freshly prepared 1-bromo-4-(bromo methyl)-2-methylbenzene 2 (13.8 g, 0.052 mol, 1.0 equi) was added drop wise and stirred at RT for 16h until completion of the reaction. The reaction mixture was diluted with EtOAc (100 mL), washed with brine solution, dried over Na$_2$SO$_4$, and then concentrated to obtain compound 4 as a pale yellow solid (18 g, 77%).

STEP-4: Preparation of 2-amino-3-(4-bromo-3-methylphenyl)propanoic acid hydrochloride: To the bromo ester compound 4 (2.0 g, 4.438 mmol, 1.0 equiv) was added 3N HCl (100 mL, 50 vol.) at RT and the resultant reaction mixture was slowly heated to 70° C. and stirred for 3h. The reaction mixture was concentrated to obtain compound 5, HCl salt, as an off-white solid (500 mg, ~45%).

STEP-5: Preparation of 3-(4-bromo-3-methylphenyl)-2-(tert-butoxycarbonyl amino) propanoic acid: To a stirred solution of compound 5 (3.0 g, 1.019 mmol, 1.0 equiv) in 1,4-dioxane (117 mL, 29 vol.) was added drop wise 1N NaOH (42 mL, 14 vol.) with stirring for 10 min at RT and (Boc)$_2$O (2.8 g, 0.0128 mmol, 1.1 equiv) at RT. Then the reaction mixture was slowly heated to reflux condition and stirred for 16h. The reaction mixture was concentrated to dryness and the obtained viscous oil was re-dissolved in EtOAc (50 mL), washed with brine solution, dried over Na$_2$SO$_4$, filtered and concentrated to dryness giving compound 6 as a pale yellow solid (2 g, 45%).

STEP-6: Preparation of tert-butyl 3-(4-bromo-3-methylphenyl)-1-(isopropylamino)-1-oxopropan-2-ylcarbamate: To a stirred solution of isopropyl amine (0.094 mL, 1.019 mmol, 1.0 eq.) in dry DCM (6.7 mL, 16.7 vol.) was added drop wise DIPEA (0.98 mL, 5.509 mmol, 5.0 eq.) with stirring for 10 min at 0° C. under N$_2$ atmosphere and then HOBt (164 mg, 1.212 mmol, 1.1 eq.). Then to the above reaction mixture were added compound 6 (400 mg, 1.1019 mmol, 1.0 eq.) and EDC·HCl (391 mg, 2.038 mmol, 2.0 eq.) subsequently. After being stirred for 16h at room temperature, it was diluted with DCM (10 mL) and quenched with 2N HCl followed by washed with saturated NaHCO$_3$, dried over Na$_2$SO$_4$, filtered and concentrated, triturated with hexane to obtain compound 7 (220 mg, 50%).

STEP-7: Preparation of tert-butyl 1-(isopropylamino)-3-(3-methyl-4-(4,4,5,5-tetramethyl-1,3,2-dioxaborolan-2-yl)phenyl)-1-oxopropan-2-ylcarbamate: To a stirred solution of 7 (200 mg, 0.502 mmol, 1.0 eq.) in a [1:1] mixture of acetonitrile and water (6 mL) were added portion wise Bis(pinacolato)diboron (153 mg, 0.603 mmol, 1.2 eq.), KOAc (99 mg, 1.006 mmol, 2.0 eq.) and Pd-118 (10.42 mg, 0.0160 mmol, 0.032 eq.) at RT under N$_2$ atmosphere. The whole reaction mixture was evacuated and back filled with N$_2$ for 2-3 times and then slowly raised to 75-80° C. for reflux condition and stirred for 16h. The reaction was cooled to RT and concentrated to obtain crude residue, which was diluted with water (10 mL) and extracted with EtOAc (2×10 mL). The combined organic layer was washed with water and brine solution and dried with anhydrous Na$_2$SO$_4$, filtered and concentrated to dryness giving compound 8 as a brown oil, which was directly used in the next reaction without any further purification (1.2 g, 63%).

STEP-8: Preparation of tert-butyl 3-(3'-hydroxy-2-methylbiphenyl-4-yl)-1-(isopropylamino)-1-oxopropan-2-ylcarbamate: To a stirred solution of boronic ester 8 (250 mg, 0.562 mmol, 1.0 eq.) in a mixture of acetonitrile (7.35 mL) and water (4.4 mL) were added portion wise KOAc (110 mg, 1.120 mmol, 2.0 eq.), 3-Bromo phenol (0.08 mL, 0.739 mmol, 1.32 eq.) and Pd-118 (11.7 mg, 0.0179, 0.032 eq.) at room temperature under N$_2$ atmosphere. The whole reaction mixture was evacuated and back filled with N2 for 2-3 times and then slowly raised to 80-90° C. for reflux condition and stirred for 24h. Slowly it was brought to RT and concentrated under reduced pressure to obtain crude residue, which was re-dissolved in EtOAc (10 mL) followed by water (10 mL) was added. Then solution of this reaction crude was extracted with EtOAc (2×10 mL). The combined organic layer was washed with water and brine solution and then concentrated under reduced pressure. The resultant crude product was purified by silica gel (60-120 mesh) column chromatography using 50-60% EtOAc/hexane to obtain compound 9 as a yellow solid (150 mg, 65%).

STEP-9: Preparation of 2-amino-3-(3'-hydroxy-2-methyl-biphenyl-4-yl)-N-isopropyl propanamide: To a solution of Boc intermediate 9 (150 mg, 0.363 mmol) in dioxane (4 mL) was added 1,4 Dioxane-HCl (1.5 mL, 10 vol.) at 0° C. under N2 atmosphere. The resultant reaction mixture was stirred for 3h at RT. After completion of reaction, concentrated to dryness and purified by preparative HPLC giving the desired compound as an off white solid (40 mg, 18%). MS calculated for [M] 312.18 and found [M+H]$^+$ 313.3.

Compound 3

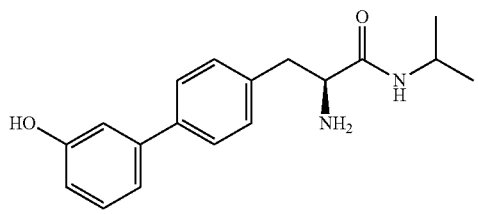 [SMILES: CC(C)NC(=O)[C@@H](N)Cc1ccc(-c2cccc(O)c2)cc1]

STEP-1: Preparation of (S)-tert-butyl 3-(4-iodophenyl)-1-(isopropylamino)-1-oxopropan-2-ylcarbamate: To a stirred solution of isopropyl amine (0.43 mL, 5.115 mmol, 1.0 eq.) in dry DCM (33.4 mL, 16.7 vol.) was added drop wise DIPEA (3.30 g, 25.575 mmol, 5.0 eq.) on stirring for 10 min at 0° C. under N2 atmosphere and then HOBt (760 mg, 5.621 mmol, 1.1 eq.) was also added lot wise for 5 min at 0° C. To this mixture were added (S)-2-(tert-butoxycarbonylamino)-3-(4-iodophenyl)propanoic acid (2.0 g, 5.115 mmol, 1.0 eq.) and EDC·HCl (1.96 g, 1.023 mmol, 2.0 eq.) subsequently. Then the reaction mixture was stirred for 16h. Reaction was monitored by TLC. The reaction mixture was diluted with DCM (10 mL) and quenched with 2N HCl followed by washed with saturated aq. NaHCO$_3$, dried over Na$_2$SO$_4$, filtered and concentrated to dryness giving 1 as a white solid (1.9 g, 86%).

STEP-2: Preparation of ((S)-tert-butyl 1-(isopropylamino)-1-oxo-3-(4-(4,4,5,5-tetramethyl-1,3,2-dioxaborolan-2-yl)phenyl)propan-2-ylcarbamate: To a stirred solution of compound 1 (1.9 g, 4.398 mmol, 1.0 eq.) in a [1:1] solvent mixture of acetonitrile and water (57 mL, 30 vol.) were added portion wise Bis(pinacolato)diboron (1.34 g, 5.277 mmol, 1.2 eq.), KOAc (0.865 g, 8.809 mmol, 2.0 eq.) and Pd-118 (91 mg, 0.1407 mmol, 0.032 eq.) at RT under N2 atmosphere. The whole reaction mixture was evacuated and back filled with N2 for 2-3 times for 30-40 sec and then slowly raised to 75-80° C. and allowed to stir at reflux for 24h. The reaction mixture was brought to RT and concentrated to dryness, diluted with water (180 mL) and extracted with EtOAc (3×50 mL). The combined organic layers were washed with brine solution and dried over anhydrous Na$_2$SO$_4$, filtered and concentrated under reduced pressure to obtain compound 2 as a brown oil, which was immediately used in next step without any further purification (1.2 g, 63%).

STEP-3: Preparation of (S)-tert-butyl 3-(3'-hydroxybiphenyl-4-yl)-1-(isopropylamino)-1-oxopropan-2-ylcarbamate: To a stirred solution of boronic ester 2 (600 mg, 1.388 mmol, 1.0 eq.) in a solvent mixture of acetonitrile (17.64 mL, 29.4 vol.) and water (10.6 mL, 17.6 vol.) were added portion wise KOAc (273 mg, 2.778 mmol, 2.0 eq.), 3-Bromo phenol (317 mg, 1.833 mmol, 1.32 eq.) and Pd-118 (30 mg, 0.044 mmol, 0.032 eq.) at rt under N2 atmosphere. The whole reaction mixture was evacuated and back filled with N2 for 2-3 times and then slowly raised to 80-90° C. to reflux and stirred for 16h. Then the reaction was cooled down to RT and diluted with water (5 mL) and extracted with EtOAc (2×40 mL). The combined organic layers were washed with brine solution, dried over anhydrous Na$_2$SO$_4$, filtered and concentrated under reduced pressure to obtain viscous light brown oil, which was further purified by silica gel (60-120 mesh) column chromatography using 5-10% MeOH/DCM to obtain compound 4 as a pale brown solid (250 mg, 63%).

STEP-4: Preparation of (S)-2-amino-3-(3'-hydroxybiphenyl-4-yl)-N-isopropylpropanamide: To the Boc intermediate 4 (400 mg, 1.0017 mmol, 1.0 eq.) was added Ether-HCl (8 mL, 20 vol.) at 0° C. under N2 atmosphere. The resultant reaction mixture was stirred for 30 min at RT. The reaction mixture was concentrated to dryness and purified by preparative HPLC to obtain the desired final product. TFA salt as an off white solid (70 mg, 23%). MS calculated for [M] 298.17 and found [M+H]$^+$ 299.3.

Biological Assays

The compounds of the present disclosure may be tested for binding to, inhibition of, and/or modulation of PCSK9 activity according to the following protocols.

Cell Culture

Cells, such as HepG2, HuH7, FL83B, or a cell line transfected with a short-hairpin PCSK9 knockdown sequence (e.g., HepG2/shPCSK9, HuH7/shPCSK9) can be cultured following routine procedures, such as those described by Benjannet et al., "Effects of the prosegment and pH on the activity of PCSK9: evidence for additional processing events" *J Biol Chem.* 285(52): 40965-40978 (2010), which is hereby incorporated by reference in its entirety.

LDLR Flow Cytometric Analysis and LDLR FACS Analysis

LDLR levels can be measured using flow cytometry or fluorescence activated cell sorting (FACS) using protocols adapted from Benjannet et al., "Effects of the prosegment and pH on the activity of PCSK9: evidence for additional processing events" *J Biol Chem.* 285(52): 40965-40978

(2010) and "Composition and Methods of Use of Small Molecules as Binding Ligands for the Modulation of Proprotein Convertase Subtilisin/Kexin Type 9 (PCSK9) Protein Activity" (WO2016029037), which are incorporated by reference in their entirety.

Cells, such as HepG2, HuH7, FL83B, or a cell line transfected with a short-hairpin PCSK9 knockdown sequence such as HepG2/shPCSK9, HuH7/shPCSK9, or FL83B/shPCSK9 are plated and cultured at 37° C. for 12-24h. Culture media is removed and replaced with fresh culture media or culture media plus a predetermined amount of recombinant PCSK9, for example a 10 nM final concentration of PCSK9. Cell culture media can be composed of DMEM (Invitrogen) with 10% fetal bovine serum (Life Technologies) supplemented with penicillin-streptomycin (Life Technologies). Cells are dosed with small molecule test compounds at doses ranging from 0 nM to 100 uM Following an incubation period of specified length, such as 6 hours, the media is removed and the cells are rinsed three times with a rinse solution (i.e., Dulbecco's phosphate buffered saline (D-PBS, Life Technologies) supplemented with 0.5% bovine serum albumin (BSA, Sigma) and 1 g/L glucose (Sigma)). The fluid is then removed, and cells are released from the plate using TrypLE Express (Life Technologies) per manufacturer's recommend procedures, such as incubation for 5-10 minutes at 37° C. The TyrpLE-Cell suspension is then transferred to 15 mL conical tubes, volume is increased to 2 mL with D-PBS supplemented with 0.5% BSA and 1 g/mL glucose, and the tubes are centrifuged at 250× gravity for 10 minutes. Following centrifugation, the supernatant is aspirated and the cell pellet is resuspended in 100 uL D-PBS containing 0.5% BSA and 1 g/mL glucose, and cells are labeled with anti-LDLR antibody per the manufacturer's recommended procedure. The cells are then pelleted by centrifugation, resuspended in 300 uL PBS and counterstained with 4',6-Diamidino-2-phenylindole (DAPI, Cayman Chemical) as a cell viability marker, other cell viability markers such as 7-aminoactinomycin D (7AAD, Life Technologies) have also been described in the art.

Cells are analyzed for both cell viability marker (dead cells) and LDLR in live cells using a flow cytometer per the manufacturer's operating manual. Cells incubated with small molecule compounds that are inhibitors of PCSK9 will be expected to show increased amounts of LDLR, relative to control (no compound) specimens, and cells incubated with small molecule compounds that are activators of PCSK9 will be expected to show decreased amounts of LDLR relative to control (no compound) specimens.

Cellular DiI-LDL Uptake Analysis

Cellular DiI-LDL uptake can be measured using protocols adapted from Benjannet et al., "Effects of the prosegment and pH on the activity of PCSK9: evidence for additional processing events" J Biol Chem. 285(52): 40965-40978 (2010) and "Composition and Methods of Use of Small Molecules as Binding Ligands for the Modulation of Proprotein Convertase Subtilisin/Kexin Type 9 (PCSK9) Protein Activity" (WO2016029037), which are incorporated by reference in their entirety.

Cells, such as HepG2, HuH7, FL83B, or a cell line transfected with a short-hairpin PCSK9 knockdown sequence such as HepG2/shPCSK9, HuH7/shPCSK9, or FL83B/shPCSK9 are plated and cultured at 37° C. for 12-24h. Culture media is removed and replaced with fresh lipoprotein-depleted culture media supplemented with 5 ug/mL of DiI-LDL (Kalen Biomedical) or lipoprotein-depleted culture media supplemented with 5 ug/mL of DiI-LDL plus a predetermined concentration of recombinant PCSK9, for example a 10 nM final concentration of PCSK9.

Lipoprotein-depleted culture media can be composed of DMEM (Invitrogen) with 10% lipoprotein-depleted fetal bovine serum (Kalen Biomedical) and supplemented with penicillin-streptomycin (Life Technologies). Cells are dosed with small molecule test compounds at doses ranging from 0 nM to 100 uM.

Following an incubation period of specified length, such as 6 hours, Hoechst 33342 (AnaSpec) stain is added to the cell media per manufacturer's instructions and incubated for a specified length (e.g., 30 minutes). The lipoprotein-depleted media is removed and cells rinsed three times with phosphate buffered saline. A final volume of phosphate buffered saline is added back to the wells. The DiI fluorescence is measured with a plate reader using an exciting wavelength of 550 nm and the resulting emission at 590 nm is measured. The Hoechst stain fluorescence is measured with a plate reader using an exciting wavelength of 355 nm and the resulting emission at 460 nm is measured.

Cells are analyzed by for both Hoechst stain (DNA content) and DiI-LDL fluorescence. Cells incubated with small molecule compounds that are inhibitors of PCSK9 will be expected to show increased amounts of DiI-LDL fluorescence, relative to control (no compound) specimens, and cells incubated with small molecule compounds that are activators of PCSK9 will be expected to show decreased amounts of DiI-LDL fluorescence relative to control (no compound) specimens.

LDL Uptake Cell-Based Assay Kit

LDL uptake and LDLR expression can also be measured in cells, such as HepG2 or HuH7 cells, using a commercial kit (Cayman Chemical Co., Catalog #10011125) and the accompanying protocols provided by the manufacturer.

Back-Scattering Interferometry Direct Binding Measurement

Direct binding can be measured using Back-Scattering Interferometry (BSI), which has been previously described in "Interferometric detection system and method" (EP 1210581), "Free solution measurement of molecular interactions by backscattering interferometry" (WO 2009039466), "Temperature-stable interferometer" (WO 2009076372), and "Improved event detection for back-scattering interferometry" (WO 2013158300); each of which are hereby incorporated by reference in their entirety.

TABLE 1

Representative Cell Activity of PCSK9 Inhibitory Compounds

| Compound # | Structure | IUPAC Chemical Name | Uptake Assay: % Inhibition of 2.5 ug/mL recombination PCSK9 @ X compound dose | LDLR Flow Assay: % Inhibition of 5.0 ug/mL recombination PCSK9 @ X compound dose |
|---|---|---|---|---|
| Compound 1 | 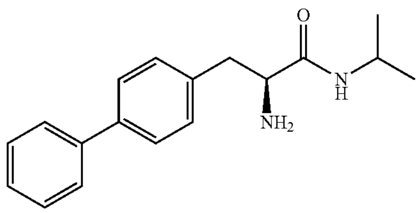 [SMILES: CC(C)NC(=O)[C@@H](N)Cc1ccc(-c2ccccc2)cc1] | (S)-3-([1,1'-biphenyl]-4-yl)-2-amino-N-isopropylpropanamide | ~15% @ 1.25 uM<br>>100% @ 10 uM | ~15% @ 1.25 uM<br>~55% @ 10 uM |
| Compound 2 | 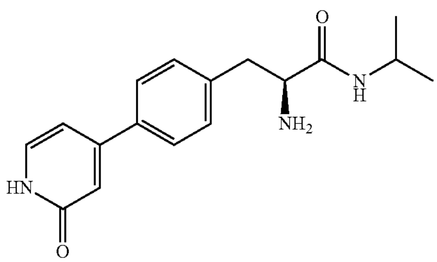 [SMILES: CC(C)NC(=O)[C@@H](N)Cc1ccc(-c2cc[nH]c(=O)c2)cc1] | (S)-2-amino-N-isopropyl-3-(4-(2-oxo-1,2-dihydropyridin-3-yl)phenyl)propanamide | ~40% @ 1.25 uM | |
| Compound 3 | 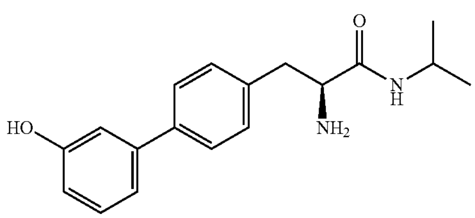 [SMILES: CC(C)NC(=O)[C@@H](N)Cc1ccc(-c2cccc(O)c2)cc1] | (S)-2-amino-3-(3'-hydroxy-[1,1'-biphenyl]-4-yl)-N-isopropylpropanamide | ~44% @ 1.25 uM | |
| Compound 4 | 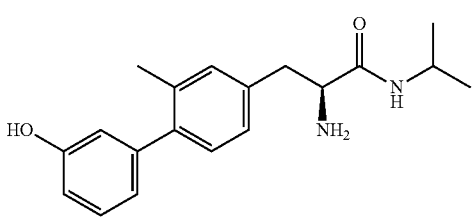 [SMILES: Cc1cc(C[C@H](N)C(=O)NC(C)C)ccc1-c1cccc(O)c1] | (S)-2-amino-3-(3'-hydroxy-2-methyl-[1,1'-biphenyl]-4-yl)-N-isopropyl propanamide | ~28% @ 1.25 uM | ~10% @ 1.25 uM |

Unless otherwise defined, all technical and scientific terms used herein have the same meaning as commonly understood by one of ordinary skill in the art to which this disclosure pertains. The disclosed embodiments illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claims.

Thus, it should be understood that although the present disclosure has been specifically disclosed by exemplary embodiments and optional features, modification, improvement and variation of the disclosed embodiments may be implemented by those skilled in the art, and that such modifications, improvements and variations are considered to be within the scope of the present disclosure and claims. The materials, methods, and examples provided here are representative of preferred embodiments, are exemplary, and are not intended as limitations on the scope of the disclosure nor as limitations on the scope of the appended claims.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

We claim:

1. A method for treating liver disease in a mammal in need thereof comprising administering to said mammal a compound of Formula I, or a pharmaceutically acceptable salt, hydrate, solvate, or tautomeric form thereof:

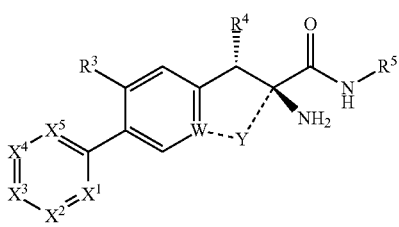

wherein $R^3$ is selected from the group consisting of H, lower alkyl, halo, haloalkyl, hydroxyalkyl, alkoxyl, and nitrile;

$R^4$ is selected from the group consisting of H and —OH;

$R^5$ is selected from the group consisting of alkyl, lower alkyl, branched alkyl, aryl-substituted alkyl, cycloalkyl, hydroxyalkyl, haloalkyl, and an amino acid, wherein the amino acid is an L- or D-isomer of the formula —$CHR^6$—CON—$R^7$;

wherein i) $R^6$ is selected from the group consisting of natural and unnatural peptide side chains; ii) $R^7$ is selected from the group consisting of alkyl, lower alkyl, branched alkyl, cycloalkyl, and heterocycle;

$X^1$ through $X^5$ are selected independently from CH, $CR^1$, $CR^2$, and N, wherein at most one of $X^1$ to $X^5$ is $CR^1$ and at most one of $X^1$ to $X^5$ is $CR^2$, and wherein $X^1$ to $X^5$ are part of an aromatic or heteroaryl ring;

$R^1$ and $R^2$ are independently selected from the group consisting of lower alkyl, halo, —OH, and amino; and W is C, CH, or N, wherein when W is C then the dashed bonds are single bonds, and W and Y join together, along with the atoms to which they are attached, to form a 5 membered ring in which Y is $CH_2$, and wherein when W is CH or N, then the dashed bonds are absent and Y is absent.

2. The method of claim 1, further comprising administering to the mammal a second active pharmaceutical.

3. The method of claim 1, comprising administering a pharmaceutical composition comprising the compound of Formula I and a pharmaceutically acceptable carrier or excipient.

4. The method of claim 3, wherein said pharmaceutical composition further comprises a second active ingredient.

5. The method of claim 1, wherein the compound is selected from:

(S)-3-([1,1'-biphenyl]-4-yl)-2-amino-N-isopropylpropanamide;

(S)-3-([1,1'-biphenyl]-4-yl)-2-amino-N-butylpropanamide;

(S)-2-amino-3-(3'-hydroxy-2-methyl-[1,1'-biphenyl]-4-yl)-N-isopropylpropanamide;

(2S,3R)-2-amino-3-hydroxy-3-(5-(3-hydroxyphenyl)-4-methylpyridin-2-yl)-N-isopropylpropanamide;

(S)-2-amino-3-(5-(3-hydroxyphenyl)pyridin-2-yl)-N-isopropylpropanamide;

(S)-2-amino-3-(5-(3-hydroxyphenyl)-4-methylpyridin-2-yl)-N-isopropylpropanamide;

(S)-2-amino-3-(2'-fluoro-5'-hydroxy-2-methyl-[1,1'-biphenyl]-4-yl)-N-isopropylpropanamide;

(R)-2-amino-N-isopropyl-5-phenyl-2,3-dihydro-1H-indene-2-carboxamide;

(S)-3-([1,1'-biphenyl]-4-yl)-2-amino-N—((S)-1-(isopropylamino)-1-oxopropan-2-yl)propanamide;

(S)-3-([1,1'-biphenyl]-4-yl)-2-amino-N—((R)-1-(isopropylamino)-1-oxopropan-2-yl)propanamide;

(R)-2-((S)-3-([1,1'-biphenyl]-4-yl)-2-aminopropanamido)-N-ethyl-3-methylbutanamide;

(S)-2-amino-3-(3'-hydroxy-[1,1'-biphenyl]-4-yl)-N—((S)-1-(isopropylamino)-1-oxopropan-2-yl)propanamide;

(R)-2-amino-5-(3-hydroxyphenyl)-N-isopropyl-6-methyl-2,3-dihydro-1H-indene-2-carboxamide;

(S)-2-amino-3-(3'-hydroxy-[1,1'-biphenyl]-4-yl)-N-isopropylpropanamide;

(S)-3-([1,1'-biphenyl]-4-yl)-2-amino-N-cyclopentylpropanamide;

(S)-3-([1,1'-biphenyl]-4-yl)-2-amino-N—((R)-1-phenylpropan-2-yl)propanamide;

(S)-3-([1,1'-biphenyl]-4-yl)-2-amino-N—((S)-1-phenylpropan-2-yl)propanamide;

(S)-2-amino-3-(2-cyano-[1,1'-biphenyl]-4-yl)-N-isopropylpropanamide;

(S)-2-amino-N-isopropyl-3-(2-methoxy-[1,1'-biphenyl]-4-yl)propanamide;

(S)-2-amino-N-isopropyl-3-(2-(trifluoromethyl)-[1,1'-biphenyl]-4-yl)propanamide;

(S)-2-amino-3-(2',3'-difluoro-[1,1'-biphenyl]-4-yl)-N-isopropylpropanamide; and (S)-2-amino-3-(2-ethyl-[1,1'-biphenyl]-4-yl)-N-isopropylpropanamide;

or a pharmaceutically acceptable salt thereof.

6. A method for increasing LDL uptake by hepatocytes in a mammal in need thereof comprising administering to said mammal a compound of Formula I, or a pharmaceutically acceptable salt, hydrate, solvate, or tautomeric form thereof:

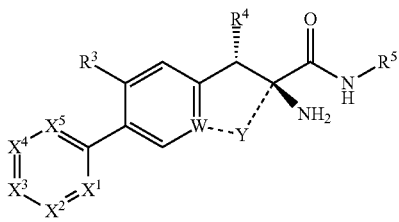

wherein
R³ is selected from the group consisting of H, lower alkyl, halo, haloalkyl, hydroxyalkyl, alkoxyl, and nitrile;
R⁴ is selected from the group consisting of H and —OH;
R⁵ is selected from the group consisting of alkyl, lower alkyl, branched alkyl, aryl-substituted alkyl, cycloalkyl, hydroxyalkyl, alkoxyalkyl, haloalkyl, and an amino acid, wherein the amino acid is an L- or D-isomer of the formula —CHR⁶—CON—R⁷;
wherein i) R⁶ is selected from the group consisting of natural and unnatural peptide side chains; ii) R⁷ is selected from the group consisting of alkyl, lower alkyl, branched alkyl, cycloalkyl, and heterocycle;
X¹ through X⁵ are selected independently from CH, CR¹, CR², and N, wherein at most one of X¹ to X⁵ is CR¹ and at most one of X¹ to X⁵ is CR², and wherein X¹ to X⁵ are part of an aromatic or heteroaryl ring;
R¹ and R² are independently selected from the group consisting of lower alkyl, halo, —OH, and amino; and
W is C, CH, or N, wherein when W is C then the dashed bonds are single bonds, and W and Y join together, along with the atoms to which they are attached, to form a 5 membered ring in which Y is CH₂, and wherein when W is CH or N, then the dashed bonds are absent and Y is absent.

7. The method of claim 6, further comprising administering to the mammal a second active pharmaceutical.

8. The method of claim 6, comprising administering a pharmaceutical composition comprising the compound of Formula I and a pharmaceutically acceptable carrier or excipient.

9. The method of claim 8, wherein said pharmaceutical composition further comprises a second active ingredient.

10. The method of claim 9, wherein said second active ingredient is selected from the group consisting of a statin, a cardiovascular drug, a metabolic drug, and an antihypertensive drug.

11. The method of claim 6, wherein the compound is selected from:
(S)-3-([1,1'-biphenyl]-4-yl)-2-amino-N-isopropylpropanamide;
(S)-3-([1,1'-biphenyl]-4-yl)-2-amino-N-butylpropanamide;
(S)-2-amino-3-(3-fluoro-4-(pyridin-4-yl)phenyl)-N-isopropylpropanamide;
(S)-2-amino-3-(3'-hydroxy-2-methyl-[1,1'-biphenyl]-4-yl)-N-isopropylpropanamide;
(2S,3R)-2-amino-3-hydroxy-3-(5-(3-hydroxyphenyl)-4-methylpyridin-2-yl)-N-isopropylpropanamide;
(S)-2-amino-3-(5-(3-hydroxyphenyl)pyridin-2-yl)-N-isopropylpropanamide;
(S)-2-amino-3-(5-(3-hydroxyphenyl)-4-methylpyridin-2-yl)-N-isopropylpropanamide;
(S)-2-amino-3-(2'-fluoro-5'-hydroxy-2-methyl-[1,1'-biphenyl]-4-yl)-N-isopropylpropanamide;
(R)-2-amino-N-isopropyl-5-phenyl-2,3-dihydro-1H-indene-2-carboxamide;
(S)-3-([1,1'-biphenyl]-4-yl)-2-amino-N—((S)-1-(isopropylamino)-1-oxopropan-2-yl)propanamide;
(S)-3-([1,1'-biphenyl]-4-yl)-2-amino-N—((R)-1-(isopropylamino)-1-oxopropan-2-yl)propanamide;
(R)-2-((S)-3-([1,1'-biphenyl]-4-yl)-2-aminopropanamido)-N-ethyl-3-methylbutanamide;
(S)-2-amino-3-(3'-hydroxy-[1,1'-biphenyl]-4-yl)-N—((S)-1-(isopropylamino)-1-oxopropan-2-yl)propanamide;
(R)-2-amino-5-(3-hydroxyphenyl)-N-isopropyl-6-methyl-2,3-dihydro-1H-indene-2-carboxamide;
(S)-2-amino-3-(3'-hydroxy-[1,1'-biphenyl]-4-yl)-N-isopropylpropanamide;
(S)-3-([1,1'-biphenyl]-4-yl)-2-amino-N-cyclopentylpropanamide;
(S)-3-([1,1'-biphenyl]-4-yl)-2-amino-N—((R)-1-phenylpropan-2-yl)propanamide;
(S)-3-([1,1'-biphenyl]-4-yl)-2-amino-N—((S)-1-phenylpropan-2-yl)propanamide;
(S)-2-amino-3-(2-cyano-[1,1'-biphenyl]-4-yl)-N-isopropylpropanamide;
(S)-2-amino-N-isopropyl-3-(2-methoxy-[1,1'-biphenyl]-4-yl)propanamide;
(S)-2-amino-N-isopropyl-3-(2-(trifluoromethyl)-[1,1'-biphenyl]-4-yl)propanamide;
(S)-2-amino-3-(2',3'-difluoro-[1,1'-biphenyl]-4-yl)-N-isopropylpropanamide; and
(S)-2-amino-3-(2-ethyl-[1,1'-biphenyl]-4-yl)-N-isopropylpropanamide;
or a pharmaceutically acceptable salt thereof.

12. A method for inducing hypocholesterolemia in a mammal in need thereof comprising administering to said mammal a compound of Formula I, or a pharmaceutically acceptable salt, hydrate, solvate, or tautomeric form thereof:

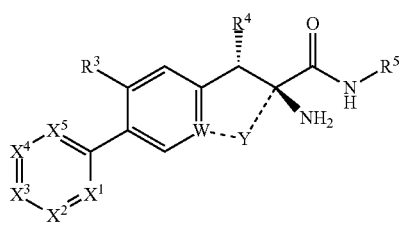

wherein
R³ is selected from the group consisting of H, lower alkyl, halo, haloalkyl, hydroxyalkyl, alkoxyl, and nitrile;
R⁴ is selected from the group consisting of H and —OH;
R⁵ is selected from the group consisting of alkyl, lower alkyl, branched alkyl, aryl-substituted alkyl, cycloalkyl, hydroxyalkyl, alkoxyalkyl, haloalkyl, and an amino acid, wherein the amino acid is an L- or D-isomer of the formula —CHR⁶—CON—R⁷;
wherein i) R⁶ is selected from the group consisting of natural and unnatural peptide side chains; ii) R⁷ is selected from the group consisting of alkyl, lower alkyl, branched alkyl, cycloalkyl, and heterocycle;
X¹ through X⁵ are selected independently from CH, CR¹, CR², and N, wherein at most one of X¹ to X⁵ is CR¹ and at most one of X¹ to X⁵ is CR², and wherein X¹ to X⁵ are part of an aromatic or heteroaryl ring;

R¹ and R² are independently selected from the group consisting of lower alkyl, halo, —OH, and amino; and W is C, CH, or N, wherein when W is C then the dashed bonds are single bonds, and W and Y join together, along with the atoms to which they are attached, to form a 5 membered ring in which Y is CH$_2$, and wherein when W is CH or N, then the dashed bonds are absent and Y is absent.

13. The method of claim 12, further comprising administering to the mammal a second active pharmaceutical.

14. The method of claim 12, comprising administering a pharmaceutical composition comprising the compound of Formula I and a pharmaceutically acceptable carrier or excipient.

15. The method of claim 14, wherein said pharmaceutical composition further comprises a second active ingredient.

16. The method of claim 15, wherein said second active ingredient is selected from the group consisting of a statin, a cardiovascular drug, a metabolic drug, and an antihypertensive drug.

17. The method of claim 12, wherein the compound is selected from:
- (S)-3-([1,1'-biphenyl]-4-yl)-2-amino-N-isopropylpropanamide;
- (S)-3-([1,1'-biphenyl]-4-yl)-2-amino-N-butylpropanamide;
- (S)-2-amino-3-(3-fluoro-4-(pyridin-4-yl)phenyl)-N-isopropylpropanamide;
- (S)-2-amino-3-(3'-hydroxy-2-methyl-[1,1'-biphenyl]-4-yl)-N-isopropylpropanamide;
- (2S,3R)-2-amino-3-hydroxy-3-(5-(3-hydroxyphenyl)-4-methylpyridin-2-yl)-N-isopropylpropanamide;
- (S)-2-amino-3-(5-(3-hydroxyphenyl)pyridin-2-yl)-N-isopropylpropanamide;
- (S)-2-amino-3-(5-(3-hydroxyphenyl)-4-methylpyridin-2-yl)-N-isopropylpropanamide;
- (S)-2-amino-3-(2'-fluoro-5'-hydroxy-2-methyl-[1,1'-biphenyl]-4-yl)-N-isopropylpropanamide;
- (R)-2-amino-N-isopropyl-5-phenyl-2,3-dihydro-1H-indene-2-carboxamide;
- (S)-3-([1,1'-biphenyl]-4-yl)-2-amino-N—((S)-1-(isopropylamino)-1-oxopropan-2-yl)propanamide;
- (S)-3-([1,1'-biphenyl]-4-yl)-2-amino-N—((R)-1-(isopropylamino)-1-oxopropan-2-yl)propanamide;
- (R)-2-((S)-3-([1,1'-biphenyl]-4-yl)-2-aminopropanamido)-N-ethyl-3-methylbutanamide;
- (S)-2-amino-3-(3'-hydroxy-[1,1'-biphenyl]-4-yl)-N—((S)-1-(isopropylamino)-1-oxopropan-2-yl)propanamide;
- (R)-2-amino-5-(3-hydroxyphenyl)-N-isopropyl-6-methyl-2,3-dihydro-1H-indene-2-carboxamide;
- (S)-2-amino-3-(3'-hydroxy-[1,1'-biphenyl]-4-yl)-N-isopropylpropanamide;
- (S)-3-([1,1'-biphenyl]-4-yl)-2-amino-N-cyclopentylpropanamide;
- (S)-3-([1,1'-biphenyl]-4-yl)-2-amino-N—((R)-1-phenylpropan-2-yl)propanamide;
- (S)-3-([1,1'-biphenyl]-4-yl)-2-amino-N—((S)-1-phenylpropan-2-yl)propanamide;
- (S)-2-amino-3-(2-cyano-[1,1'-biphenyl]-4-yl)-N-isopropylpropanamide;
- (S)-2-amino-N-isopropyl-3-(2-methoxy-[1,1'-biphenyl]-4-yl)propanamide;
- (S)-2-amino-N-isopropyl-3-(2-(trifluoromethyl)-[1,1'-biphenyl]-4-yl)propanamide;
- (S)-2-amino-3-(2',3'-difluoro-[1,1'-biphenyl]-4-yl)-N-isopropylpropanamide; and
- (S)-2-amino-3-(2-ethyl-[1,1'-biphenyl]-4-yl)-N-isopropylpropanamide;

or a pharmaceutically acceptable salt thereof.

* * * * *

SEQUENCE LISTING

```
<160> NUMBER OF SEQ ID NOS: 1

<210> SEQ ID NO 1
<211> LENGTH: 692
<212> TYPE: PRT
<213> ORGANISM: Homo sapiens

<400> SEQUENCE: 1

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
            35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
                100                 105                 110

His Val Phe His Gly Leu Leu Pro Gly Phe Leu Val Lys Met Ser Gly
            115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270
```

```
Lys Ser Gln Leu Val Gln Pro Val Gly Pro Leu Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
                485                 490                 495

Gly Glu Arg Met Glu Ala Gln Gly Gly Lys Leu Val Cys Arg Ala His
            500                 505                 510

Asn Ala Phe Gly Gly Glu Gly Val Tyr Ala Ile Ala Arg Cys Cys Leu
        515                 520                 525

Leu Pro Gln Ala Asn Cys Ser Val His Thr Ala Pro Pro Ala Glu Ala
    530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
        595                 600                 605

Lys Val Lys Glu His Gly Ile Pro Ala Pro Gln Glu Gln Val Thr Val
    610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655
```

```
Arg Ser Arg Asp Val Ser Thr Thr Gly Ser Thr Ser Glu Gly Ala Val
            660                 665                 670

Thr Ala Val Ala Ile Cys Cys Arg Ser Arg His Leu Ala Gln Ala Ser
            675                 680                 685

Gln Glu Leu Gln
    690
```